(12) United States Patent
Kallok et al.

(10) Patent No.: US 12,295,612 B2
(45) Date of Patent: *May 13, 2025

(54) ATHERECTOMY DEVICES AND METHODS

(71) Applicant: Cardio Flow, Inc., St. Paul, MN (US)

(72) Inventors: Michael Kallok, St. Paul, MN (US); Cassandra Ann Piippo Svendsen, Blaine, MN (US); Paul Joseph Robinson, Mahtomedi, MN (US); Charles Anthony Plowe, Blaine, MN (US); Albert Selden Benjamin, St Paul, MN (US)

(73) Assignee: Cardio Flow, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/380,926

(22) Filed: Oct. 17, 2023

(65) Prior Publication Data

US 2024/0074783 A1 Mar. 7, 2024

Related U.S. Application Data

(63) Continuation of application No. 17/576,278, filed on Jan. 14, 2022, now Pat. No. 11,812,988, which is a
(Continued)

(51) Int. Cl.
*A61B 17/3207* (2006.01)
*A61B 17/32* (2006.01)

(52) U.S. Cl.
CPC ........... *A61B 17/320725* (2013.01); *A61B 17/320758* (2013.01); *A61B 2017/320008* (2013.01);
(Continued)

(58) Field of Classification Search
CPC ........ A61B 17/3207; A61B 17/320725; A61B 17/320758; A61B 2017/32004;
(Continued)

(56) References Cited

U.S. PATENT DOCUMENTS 1,431,416 A 10/1922 Parsons
1,916,085 A 6/1933 Summers
(Continued)

FOREIGN PATENT DOCUMENTS

CN 104955406 9/2015
DE 20305953 8/2003
(Continued)

OTHER PUBLICATIONS

"Declaration of Dr. Morten Olgaard Jensen, " IPIPR2018-01658, Exhibit 1002, dated Sep. 4, 2018.
(Continued)

*Primary Examiner* — Ryan J. Severson
(74) *Attorney, Agent, or Firm* — Fish & Richardson P.C.

(57) ABSTRACT

Rotational atherectomy devices and systems can remove or reduce stenotic lesions in implanted grafts by rotating one or more abrasive elements within the graft. The abrasive elements can be attached to a distal portion of an elongate flexible drive shaft that extends from a handle assembly that includes a driver for rotating the drive shaft. In particular implementations, individual abrasive elements are attached to the drive shaft at differing radial angles in comparison to each other (e.g., configured in a helical array). The centers of mass of the abrasive elements can define a path that fully or partially spirals around the drive shaft.

16 Claims, 9 Drawing Sheets

Related U.S. Application Data continuation of application No. 16/733,514, filed on Jan. 3, 2020, now Pat. No. 11,253,290, which is a continuation of application No. 16/196,894, filed on Nov. 20, 2018, now Pat. No. 10,524,826, which is a continuation of application No. 16/008,136, filed on Jun. 14, 2018, now Pat. No. 11,147,582.

(52) U.S. Cl.
CPC ............. *A61B 2017/320716* (2013.01); *A61B 2017/320733* (2013.01)

(58) Field of Classification Search
CPC ....... A61B 2017/320008; A61B 2017/320716; A61B 2017/320733; A61B 2017/320741; A61B 2017/320766
See application file for complete search history.

(56) References Cited

U.S. PATENT DOCUMENTS

| | | |
|---|---|---|
| 2,495,316 A | 1/1950 | Clark |
| 3,929,129 A | 12/1975 | Archambault |
| 4,445,509 A | 5/1984 | Auth |
| 4,445,892 A | 5/1984 | Hussein et al. |
| 4,620,320 A | 10/1986 | Sullivan |
| 4,646,736 A | 3/1987 | Auth |
| 4,762,130 A | 8/1988 | Fogarty et al. |
| 4,772,258 A | 9/1988 | Marangoni et al. |
| 4,784,636 A | 11/1988 | Rydell |
| 4,870,953 A | 10/1989 | DonMicheal et al. |
| 4,887,469 A | 12/1989 | Shoptaw |
| 4,931,635 A | 6/1990 | Toyama |
| 4,950,238 A | 8/1990 | Sullivan |
| 4,990,134 A | 2/1991 | Auth |
| 5,014,681 A | 5/1991 | Neeman et al. |
| 5,100,425 A | 5/1992 | Fischell et al. |
| 5,127,902 A | 7/1992 | Fischell et al. |
| 5,181,920 A | 1/1993 | Mueller et al. |
| 5,213,576 A | 5/1993 | Abiuso |
| 5,213,577 A | 5/1993 | Kratzer |
| 5,217,474 A | 6/1993 | Zacca et al. |
| 5,242,460 A | 9/1993 | Klein et al. |
| 5,250,059 A | 10/1993 | Andreas et al. |
| 5,250,060 A | 10/1993 | Carbo et al. |
| 5,273,526 A | 12/1993 | Dance et al. |
| 5,308,354 A | 5/1994 | Zacca et al. |
| 5,312,427 A | 5/1994 | Shturman |
| 5,314,407 A | 5/1994 | Auth |
| 5,314,438 A | 5/1994 | Shturman |
| 5,342,292 A | 8/1994 | Nita et al. |
| 5,361,285 A | 10/1994 | Formanek |
| 5,370,653 A | 12/1994 | Cragg |
| 5,435,009 A | 7/1995 | Schild |
| 5,458,575 A | 10/1995 | Wang |
| 5,490,859 A | 2/1996 | Mische et al. |
| 5,512,044 A | 4/1996 | Duer |
| 5,556,389 A | 9/1996 | Liprie |
| 5,584,843 A | 12/1996 | Wulfman |
| 5,649,941 A | 7/1997 | Lary |
| 5,681,336 A | 10/1997 | Clement |
| 5,730,717 A | 5/1998 | Gelbfish |
| 5,766,192 A | 6/1998 | Zacca et al. |
| 5,771,895 A | 6/1998 | Slager |
| 5,816,923 A | 10/1998 | Milo |
| 5,836,957 A | 11/1998 | Schulz |
| 5,843,103 A | 12/1998 | Wulfman |
| 5,868,708 A | 2/1999 | Hart |
| 5,893,857 A | 4/1999 | Shturman |
| 6,010,533 A | 1/2000 | Pope |
| 6,015,420 A | 1/2000 | Wulfman |
| 6,022,363 A | 2/2000 | Walker |
| 6,024,749 A | 2/2000 | Shturman |
| 6,030,401 A | 2/2000 | Marino |
| 6,066,152 A | 5/2000 | Strauss |
| 6,077,282 A | 6/2000 | Shturman |
| 6,096,054 A | 8/2000 | Wyzgala |
| 6,132,444 A | 10/2000 | Shturman |
| 6,135,982 A | 10/2000 | Campbell |
| 6,146,395 A | 11/2000 | Kanz |
| 6,152,911 A | 11/2000 | Giannoble |
| 6,156,048 A | 12/2000 | Wulfman |
| 6,217,595 B1 | 4/2001 | Shturman |
| 6,241,706 B1 | 6/2001 | Leschinsky |
| 6,270,465 B1 | 8/2001 | Keith |
| 6,416,526 B1 | 7/2002 | Wyzgala |
| 6,482,216 B1 | 11/2002 | Hiblar et al. |
| 6,485,500 B1 | 11/2002 | Kokish |
| 6,491,660 B2 | 12/2002 | Guo |
| 6,494,890 B1 | 12/2002 | Shturman |
| 6,497,711 B1 | 12/2002 | Plaia |
| 6,565,588 B1 | 5/2003 | Clement |
| 6,626,861 B1 | 9/2003 | Hart |
| 6,685,718 B1 | 2/2004 | Wyzgala |
| 6,733,513 B2 | 5/2004 | Boyle |
| 6,805,485 B2 | 10/2004 | Hogan |
| 6,852,118 B2 | 2/2005 | Shturman |
| 6,955,661 B1 | 10/2005 | Herweck |
| 7,252,674 B2 | 8/2007 | Wyzgala |
| 7,666,202 B2 | 2/2010 | Prudnikov et al. |
| 7,766,049 B2 | 8/2010 | Miller |
| 8,109,954 B2 | 2/2012 | Shturman |
| 8,109,955 B2 | 2/2012 | Shturman |
| 8,137,369 B2 | 3/2012 | Shturman |
| 8,142,458 B2 | 3/2012 | Shturman |
| 8,147,507 B2 | 4/2012 | Shturman |
| 8,157,825 B2 | 4/2012 | Shturman |
| 8,177,801 B2 | 5/2012 | Kallok et al. |
| 8,348,965 B2 | 1/2013 | Prudnikov |
| 8,353,923 B2 | 1/2013 | Shturman |
| 8,388,636 B2 | 3/2013 | Shturman |
| 8,388,637 B2 | 3/2013 | Shturman |
| 8,454,638 B2 | 6/2013 | Shturman |
| 8,465,510 B2 | 6/2013 | Shturman |
| 8,496,678 B2 | 7/2013 | Shturman |
| 8,500,764 B2 | 8/2013 | Shturman |
| 8,500,765 B2 | 8/2013 | Shturman |
| 8,597,313 B2 | 12/2013 | Thatcher |
| 8,628,550 B2 | 1/2014 | Narveson |
| 8,663,195 B2 | 3/2014 | Shturman |
| 8,663,260 B2 | 3/2014 | Shturman |
| 8,663,261 B2 | 3/2014 | Shturman |
| 9,089,362 B2 | 7/2015 | Shturman |
| 8,936,589 B2 | 10/2015 | Shturman |
| 9,192,405 B2 | 11/2015 | Shturman |
| 9,211,138 B2 | 12/2015 | Shturman |
| 9,237,903 B2 | 1/2016 | Shturman |
| 9,289,230 B2 | 3/2016 | Cambronne |
| 9,333,006 B2 | 5/2016 | Shturman |
| 9,364,256 B2 | 6/2016 | Shturman |
| 9,387,006 B2 | 7/2016 | Shturman |
| 9,597,109 B2 | 3/2017 | Shturman |
| 9,737,329 B2 | 8/2017 | Shturman |
| 9,757,144 B2 | 9/2017 | Shturman |
| 9,788,853 B2 | 10/2017 | Robinson et al. |
| 9,883,886 B2 | 2/2018 | Shturman |
| 10,327,803 B2 | 6/2019 | Robinson et al. |
| 10,335,187 B2 | 7/2019 | Benjamin |
| 10,368,901 B2 | 8/2019 | Robinson et al. |
| 10,441,312 B2 | 10/2019 | Benjamin |
| 10,463,390 B1 | 11/2019 | Robinson |
| 10,470,794 B2 | 11/2019 | Robinson et al. |
| 10,478,215 B2 | 11/2019 | Robinson et al. |
| 10,478,216 B2 | 11/2019 | Robinson et al. |
| 10,478,217 B2 | 11/2019 | Robinson et al. |
| 10,499,946 B2 | 12/2019 | Robinson et al. |
| 10,517,631 B2 | 12/2019 | Cambronne |
| 10,517,634 B2 | 12/2019 | Benjamin |
| 10,524,826 B1 | 1/2020 | Benjamin |
| 10,639,062 B2 | 5/2020 | Svendsen et al. |
| 10,639,063 B2 | 5/2020 | Svendsen et al. |
| 10,639,064 B2 | 5/2020 | Svendsen et al. |
| 2002/0007190 A1 | 1/2002 | Wulfman |
| 2002/0013600 A1 | 1/2002 | Scribner |

(56) References Cited

U.S. PATENT DOCUMENTS

| | | |
|---|---|---|
| 2002/0029056 A1 | 3/2002 | Hall |
| 2002/0082547 A1 | 6/2002 | Deniega |
| 2002/0099367 A1 | 7/2002 | Guo |
| 2002/0138088 A1 | 9/2002 | Nash |
| 2002/0151918 A1 | 10/2002 | Lafontaine |
| 2002/0188276 A1 | 12/2002 | Evans |
| 2003/0078606 A1 | 4/2003 | Lafontaine |
| 2003/0114869 A1 | 6/2003 | Nash |
| 2003/0125756 A1 | 7/2003 | Shturman |
| 2003/0139689 A1 | 7/2003 | Shturman |
| 2003/0199889 A1 | 10/2003 | Kanz |
| 2004/0098014 A1 | 5/2004 | Flugelman |
| 2004/0158270 A1 | 8/2004 | Wyzgala |
| 2005/0154416 A1 | 7/2005 | Herweck |
| 2005/0209615 A1 | 9/2005 | Prudnikov |
| 2005/0228402 A1 | 10/2005 | Hofmann |
| 2005/0240146 A1 | 10/2005 | Nash |
| 2005/0245864 A1 | 11/2005 | O'Brien |
| 2005/0256461 A1 | 11/2005 | DiFiore |
| 2006/0189929 A1 | 8/2006 | Lary |
| 2006/0258976 A1 | 11/2006 | Shturman et al. |
| 2007/0007190 A1 | 1/2007 | Pethke |
| 2007/0066888 A1 | 3/2007 | Maschke |
| 2008/0004643 A1 | 1/2008 | Schur |
| 2008/0097498 A1 | 4/2008 | Shimizu |
| 2008/0119946 A1 | 5/2008 | Nugent et al. |
| 2008/0161840 A1 | 7/2008 | Osiroff |
| 2008/0306498 A1 | 12/2008 | Thatcher |
| 2008/0319415 A1 | 12/2008 | Shturman |
| 2009/0018564 A1 | 1/2009 | Shturman |
| 2009/0069829 A1 | 3/2009 | Shturman |
| 2009/0105736 A1 | 4/2009 | Prudnikov |
| 2009/0182359 A1 | 7/2009 | Shturman |
| 2009/0264908 A1 | 10/2009 | Kallok |
| 2009/0312777 A1 | 12/2009 | Shturman |
| 2009/0318942 A1 | 12/2009 | Shturman |
| 2009/0326568 A1 | 12/2009 | Shturman |
| 2010/0010522 A1 | 1/2010 | Shturman |
| 2010/0049226 A1 | 2/2010 | Shturman |
| 2010/0211088 A1 | 8/2010 | Narveson |
| 2011/0009888 A1 | 1/2011 | Shturman |
| 2011/0054332 A1 | 3/2011 | Shturman |
| 2011/0213391 A1 | 9/2011 | Rivers et al. |
| 2012/0178986 A1 | 1/2012 | Campbell et al. |
| 2012/0035633 A1 | 2/2012 | Shturman |
| 2012/0109170 A1 | 5/2012 | Shturman |
| 2012/0150207 A1 | 6/2012 | Shturman |
| 2012/0172903 A1 | 7/2012 | Shturman |
| 2012/0191113 A1 | 7/2012 | Shturman |
| 2013/0178881 A1 | 7/2013 | Shturman |
| 2013/0204280 A1 | 8/2013 | Shturman |
| 2013/0245654 A1 | 9/2013 | Shturman |
| 2013/0274773 A1 | 10/2013 | Shturman |
| 2013/0296904 A1 | 11/2013 | Shturman |
| 2013/0296905 A1 | 11/2013 | Shturman |
| 2013/0310589 A1 | 11/2013 | Ripley |
| 2013/0310859 A1 | 11/2013 | Shturman |
| 2013/0333365 A1 | 12/2013 | Silet |
| 2014/0081298 A1 | 3/2014 | Cambronne |
| 2014/0180317 A1 | 6/2014 | Shturman |
| 2014/0180318 A1 | 6/2014 | Shturman |
| 2014/0180319 A1 | 6/2014 | Shturman |
| 2014/0296888 A1 | 10/2014 | Schur |
| 2015/0080795 A1 | 3/2015 | Mattison |
| 2015/0094733 A1 | 4/2015 | Shiber |
| 2015/0196320 A1 | 7/2015 | Robinson |
| 2016/0199093 A1 | 7/2016 | Cambronne |
| 2017/0290603 A1 | 10/2017 | Svendsen et al. |
| 2018/0064464 A1 | 3/2018 | Robinson et al. |
| 2018/0235652 A1 | 8/2018 | Benjamin |
| 2019/0083126 A1 | 3/2019 | Benjamin et al. |

FOREIGN PATENT DOCUMENTS

| | | |
|---|---|---|
| EP | 0419154 | 3/1991 |
| EP | 0479433 | 4/1992 |
| EP | 0820729 | 1/1998 |
| EP | 1405797 | 4/2004 |
| EP | 1820458 | 8/2007 |
| EP | 3105978 | 12/2016 |
| FR | 1595757 | 6/1970 |
| GB | 854573 | 11/1960 |
| GB | 2039208 | 8/1980 |
| GB | 2271060 | 4/1994 |
| GB | 2357573 | 6/2001 |
| GB | 2426458 | 11/2006 |
| WO | WO 1997/14470 | 4/1997 |
| WO | WO 1998/50101 | 11/1998 |
| WO | WO 1999/44513 | 9/1999 |
| WO | WO 2001/15759 | 3/2001 |
| WO | WO 2002/09599 | 2/2002 |
| WO | WO 2003/061457 | 7/2003 |
| WO | WO 2006/126076 | 11/2006 |
| WO | WO 2006/126175 | 11/2006 |
| WO | WO 2006/126176 | 11/2006 |
| WO | WO 2008/006704 | 1/2008 |
| WO | WO 2014/042752 | 3/2014 |

OTHER PUBLICATIONS

"Declaration of Dr. Morten Olgaard Jensen," IPR2018-01549, Exhibit 1002, dated Aug. 15, 2018.
"Declaration of Kristina Rouw, Ph.D," IPR2018-01549, Exhibit 2001, dated Nov. 29, 2018.
"Declaration of Kristina Rouw, Ph.D," IPR2018-01658, Exhibit 2001, dated Dec. 10, 2018.
"Patent Owner's Preliminary Response," IPR2018-01549, Paper 8, dated Nov. 29, 2018.
"Patent Owner's Preliminary Response," IPR2018-01658, Paper 6, dated Dec. 11, 2018.
"Petition For Inter Partes Review of U.S. Pat. No. 9,089,362 Under 35 U.S.C. § 312 and 37 C.F.R. § 42.104," *Cardiovascular Systems, Inc. v. Cardio Flow, Inc.*, IPR2018-01658, Paper 1, dated Sep. 5, 2018.
"Petition For Inter Partes Review of U.S. Pat. No. 9,788,853 Under 35 U.S.C. § 312 and 37 C.F.R. § 42.104," *Cardiovascular Systems, Inc. v. Cardio Flow, Inc.*, IPR2018-01549, Paper 1, dated Aug. 17, 2018.
Declaration of Aleksey Filippov, Apr. 23, 2007, 1 page.
Declaration of Dmitri Prudnikov, Apr. 23, 2007, 1 page.
European Search Report in Application No. 15737946.2, dated Aug. 1, 2017, 8 pages.
Excerpt from Deposition of Dmitri Prudnikov, Mar. 5, 2008, 7 pages.
Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.
Invitation To Pay Additional Fees And, Where Applicable, Protest Fee in Application No. PCT/US2017/26179, mailed on Jul. 6, 2017, 2 pages.
PCT international Preliminary Report on Patentability in International Appln. No. PCT/EP2010/054548, dated Oct. 4, 2011, 8 pages.
PCT international Preliminary Report on Patentability in International Appln. No. PCT/EP2010/054550, dated Oct. 4, 2011, 7 pages.
PCT International Preliminary Report on Patentability, in International Application No. PCT/US2015/011212, dated Jul. 19, 2016, 8 pages.
PCT International Search Report and Written Opinion in International Application No. PCT/US2015/011212, dated May 6, 2015.
PCT International Search Report and Written Opinion in International Application No. PCT/US2017/26179, dated Oct. 4, 2017, 15 pages.

(56) References Cited

OTHER PUBLICATIONS

PCT International Search Report and Written Opinion in International Application No. PCT/US2018/019238, dated May 8, 2018, 16 pages.
PCT International Search Report corresponding to International Application No. PCT/EP2007/056516, dated Oct. 17, 2007, 3 pages.
PCT International Search Report in International Application No. PCT/EP2007/062777, dated Apr. 9, 2008, 2 pages.
PCT International Search Report in International Appln. No. PCT/EP2007/056499, dated Nov. 5, 2007, 3 pages.
PCT International Search Report in International Appln. No. PCT/EP2007/056500, dated Dec. 11, 2007, 6 pages.
PCT International Search Report, in International Appln. No. PCT/EP2008/065986, dated Feb. 26, 2009, 3 pages.
Yevzlin, et al., "ASDIN Original Investigations: How I Do It: Directional Atherectomy for In-Stent Restenosis of a PTFE Arteriovenous Graft," Seminars in Dialysis, 2008, 21(3):266-268.

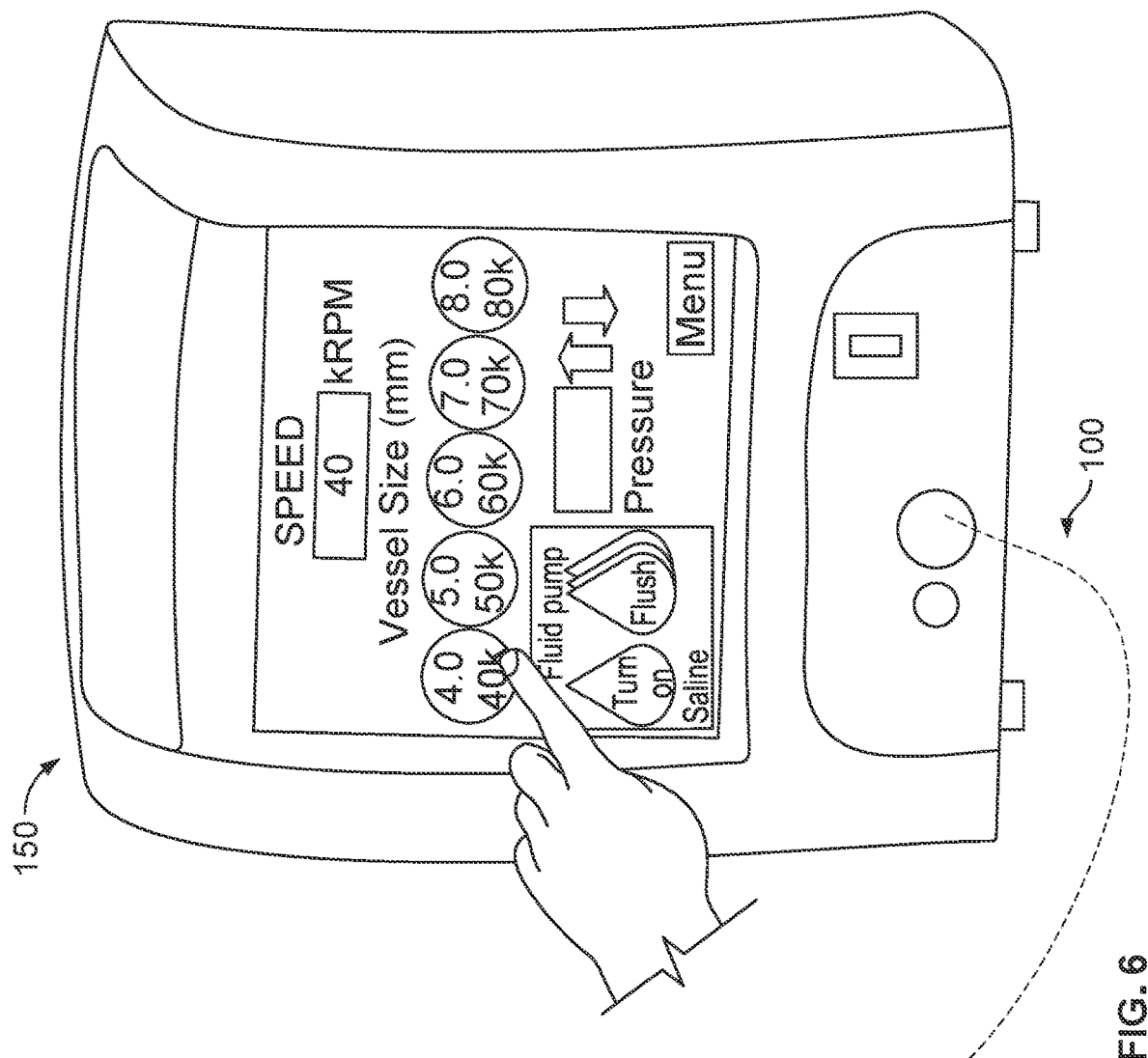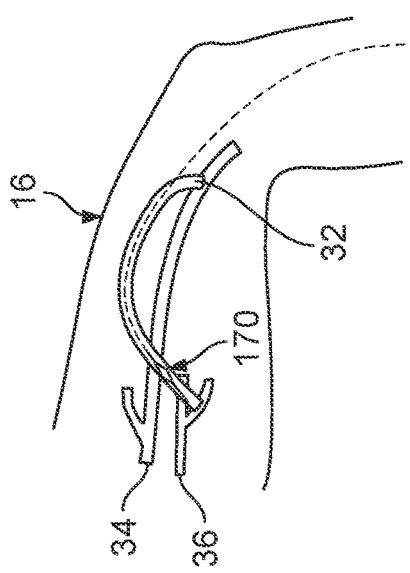
FIG. 6

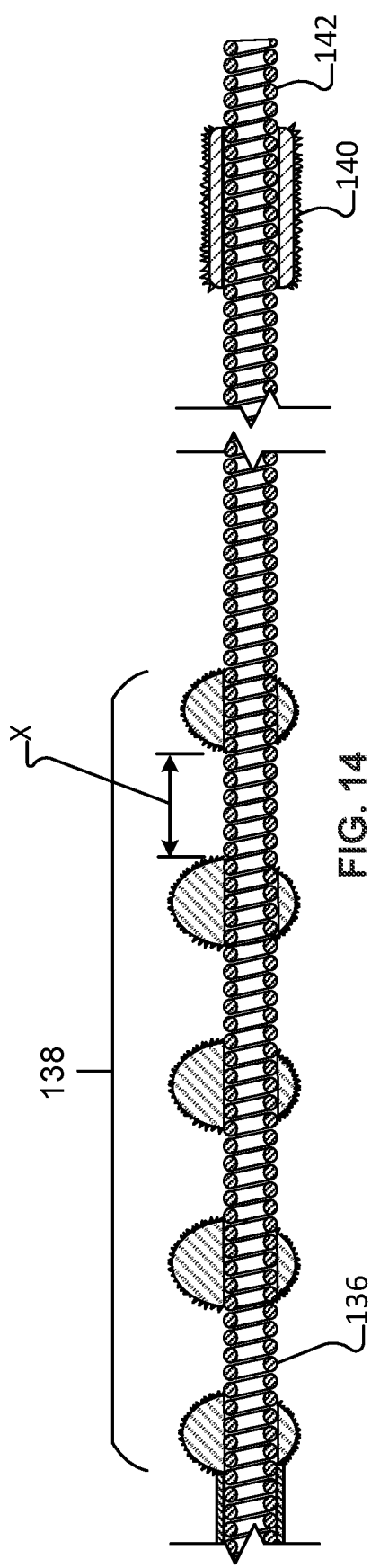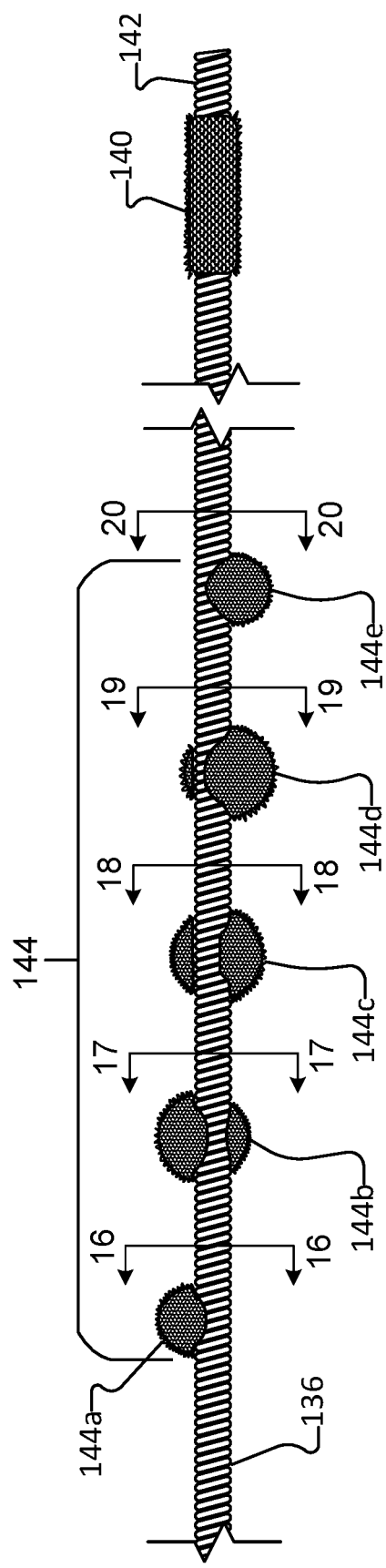

ion Ser. No. 17/576,278, filed on Jan. 14, 2022, which is a
ATHERECTOMY DEVICES AND METHODS

CLAIM OF PRIORITY

This application is a continuation of U.S. patent application Ser. No. 17/576,278, filed on Jan. 14, 2022, which is a continuation of U.S. application Ser. No. 16/733,514 filed on Jan. 3, 2020 (now U.S. Pat. No. 11,253,290), which is a continuation of U.S. patent application Ser. No. 16/196,894 filed on Nov. 20, 2018 (now U.S. Pat. No. 10,524,826), which is a continuation of U.S. patent application Ser. No. 16/008,136, filed on Jun. 14, 2018 (now U.S. Pat. No. 11,147,582, the entire contents of which are hereby incorporated by reference.

TECHNICAL FIELD

This document relates to rotational atherectomy devices and systems for removing or reducing stenotic lesions in blood vessels and/or arteriovenous grafts, for example, by rotating an abrasive element within the vessel to partially or completely remove the stenotic lesion material.

BACKGROUND

Blood flow through the peripheral arteries (e.g., iliac, femoral, renal etc.), can be affected by the development of atherosclerotic blockages. Peripheral artery disease (PAD) can be serious because without adequate blood flow, the kidneys, legs, arms, and feet may suffer irreversible damage. Left untreated, the tissue can die or harbor infection.

Patients that have kidneys that do not function properly may require hemodialysis to purify the blood of the patient. To gain access to the blood for hemodialysis, an arteriovenous fistula or a graft can be used to connect an artery and a vein. Similar to blood vessels, fistulas and/or grafts can become clogged with plaque.

SUMMARY

This document relates to rotational atherectomy devices, systems, and methods for removing or reducing stenotic lesions in an implanted graft (e.g., a synthetic arteriovenous (AV) graft) by rotating one or more abrasive elements to abrade and breakdown the lesion. Vascular access stenosis is a common issue found in hemodialysis patients. In various embodiments, a graft can be implanted into a hemodialysis patient to access blood vessels capable of providing rapid extracorporeal blood flow during hemodialysis. The implanted graft may be prone to vascular access stenosis, which forms fibrous plaque-like lesions within the lumen of the graft and extending into the native artery and vein attached to the graft. Stenotic lesions that typically develop in association with the implanted graft can contain non-calcified neointimal hyperplasia and may lead to thrombosis and graft occlusion.

Some embodiments of the systems and devices provided herein can abrade stenotic lesions in the grafts by rotating the abrasive element(s) according to a stable and predictable orbiting profile. In some embodiments, the abrasive element(s) are attached to a distal portion of an elongate flexible drive shaft that extends from a handle assembly. In particular embodiments, a rotational atherectomy device comprises an elongate flexible drive shaft with multiple eccentric abrasive elements that are attached to the drive shaft, and one or more stability elements are attached to the drive shaft such that at least one stability element is distal of the abrasive element.

Optionally, the stability elements have a center of mass that are axially aligned with a central longitudinal axis of the drive shaft while the eccentric abrasive element(s) has(have) a center(s) of mass that is(are) axially offset from central longitudinal axis of the drive shaft.

In some embodiments, multiple abrasive elements are coupled to the drive shaft and are offset from each other around the drive shaft such that the centers of the abrasive elements are disposed at differing radial angles from the drive shaft in relation to each other. For example, in some embodiments a path defined by the centers of mass of the abrasive elements defines a spiral around a length of the central longitudinal axis of the drive shaft. A flexible polymer coating may surround at least a portion of the drive shaft, including the stability element(s) in some embodiments. Also, in some optional embodiments, a distal extension portion of the drive shaft may extend distally beyond the distal-most stability element.

In one aspect, this disclosure is directed to a method for performing rotational atherectomy to remove stenotic lesion material from an arteriovenous graft of a patient. The method includes delivering a rotational atherectomy device into the arteriovenous graft. The rotational atherectomy device includes an elongate flexible drive shaft that includes a torque-transmitting coil and defines a longitudinal axis, the drive shaft being configured to rotate about the longitudinal axis, and a helical array of abrasive elements attached to a distal end portion of the drive shaft, each of the abrasive elements having a center of mass that is offset from the longitudinal axis, the centers of mass of the abrasive elements arranged along a path that spirals around the longitudinal axis. The method further includes rotating the drive shaft about the longitudinal axis such that the abrasive elements orbit around the longitudinal axis.

In another aspect, this disclosure is directed to a method for performing rotational atherectomy to remove stenotic lesion material from an arteriovenous graft of a patient. The method can include delivering a rotational atherectomy device into the arteriovenous graft. The rotational atherectomy device can include an elongate flexible drive shaft that includes a torque-transmitting coil and defines a longitudinal axis, the drive shaft being configured to rotate about the longitudinal axis, and first and second abrasive elements attached to a distal end portion of the drive shaft and each having a center of mass offset from the longitudinal axis, the center of mass of the first abrasive element being offset from the longitudinal axis at a first radial angle, the center of mass of the second abrasive element being offset from the longitudinal axis at a second radial angle that differs from the first radial angle. The method further includes rotating the drive shaft about the longitudinal axis such that the abrasive elements orbit around the longitudinal axis.

One or more of the methods can further include the embodiments described herein. In some embodiments, the method can include translationally moving the drive shaft along the longitudinal axis. The method can include modifying a speed of the drive shaft. Modifying the speed of the drive shaft can include modifying a diameter of rotation. In some embodiments, delivering the rotational atherectomy device can include delivering the rotational atherectomy device with a distal portion of the rotational atherectomy device positioned toward a vein of the patient. Delivering the rotational atherectomy device can include delivering the rotational atherectomy device with a distal portion of the rotational atherectomy device positioned toward an artery of the patient to treat a lesion at an arterial anastomosis. In some embodiments, the method can further include inflating an inflatable member on the rotational atherectomy device. In some embodiments, the rotational atherectomy device can further include a distal stability element affixed to the drive shaft and having a center of mass aligned with the longitudinal axis, the distal stability element distally spaced apart from the plurality of abrasive elements.

In yet another aspect, this disclosure is directed to a device for performing rotational atherectomy to remove stenotic lesion material from an arteriovenous graft of a patient. The device includes means for causing rotation along a longitudinal axis of the device, a first means for removing stenotic lesion material from the arteriovenous graft of the patient, the first means having a first center of mass offset from the longitudinal axis at a first radial angle, a second means for removing stenotic lesion material from the arteriovenous graft of the patient, the second means having a second center of mass offset from the longitudinal axis at a second radial angle that differs from the first radial angle, and means for mounting the means for transmitting, the first means, and the second means.

In some embodiments, the device can further include a third means for removing stenotic lesion material from the arteriovenous graft of the patient, the third means having a third center of mass offset from the longitudinal axis at a third radial angle that differs from the first radial angle and the second radial angle. In some embodiments, the second radial angle differs from the first radial angle by at least 15 degrees, and the third radial angle differs from the first radial angle and the second radial angle by at least 15 degrees. In some embodiments, a proximal-most one of the means for removing stenotic lesion material and a distal-most means for removing stenotic lesion material are each smaller than intermediate ones of the means for removing stenotic lesion material. In some embodiments, the means for stabilizing include means for removing stenotic lesion material. In some embodiments, the device further includes means for receiving a guidewire along the longitudinal axis. In some embodiments, the device also includes means for causing translational movement of the device along the longitudinal axis. In some embodiments, the device includes means for extending a distal portion of the device. In some embodiments, the device further includes means for stabilizing the means for mounting, the means for stabilizing having a center of mass aligned with the longitudinal axis.

Some of the embodiments described herein may provide one or more of the following advantages. First, some embodiments of the rotational atherectomy devices and systems operate with a stable and predictable rotary motion profile for an atherectomy procedure applied to an implanted graft (e.g., synthetic AV graft) for the removal of stenotic plaque-like lesions from within the graft. That is, when the device is being rotated in operation, the eccentric abrasive element(s) follows a predefined, consistent orbital path (offset from an axis of rotation of the device) while the stability element(s) and other portions of the device remain on or near to the axis of rotation for the drive shaft in a stable manner. This predictable orbital motion profile can be attained by the use of design features including, but not limited to, stability element(s) that have centers of mass that are coaxial with the longitudinal axis of the drive shaft, a polymeric coating on at least a portion of the drive shaft, a distal-most drive shaft extension portion, and the like. Some embodiments of the rotational atherectomy devices and systems provided herein may include one or more of such design features.

Second, the rotational atherectomy devices provided herein may include a distal stability element that has an abrasive outer surface that allows a rotational atherectomy device, when being advanced within an implanted graft, to treat plaque-like lesions that occlude or substantially occlude the graft. In such applications, the abrasive outer surface on the distal stability element may help facilitate passage of the distal stability element through plaque-like lesions that occlude or substantially occlude the graft. In some such cases, the drive shaft may be used to rotate the distal stability element to help facilitate boring of the distal stability element through such lesions in a drill-like fashion.

Third, some embodiments of the rotational atherectomy devices and systems provided herein can be used to treat various graft sizes (e.g., large-diameter grafts having an internal diameter that is multiple time greater than the outer diameter of the abrasive element) while, in some embodiments, using a small introducer sheath size for delivery of the devices and systems. In other words, in some embodiments the rotating eccentric abrasive element(s) traces an orbital path that is substantially larger than the outer diameter of the rotational atherectomy device in the non-rotating state. This feature improves the ability of the rotational atherectomy devices provided herein to treat, in some embodiments, very large grafts while still fitting within a small introducer size. In some embodiments, this feature can be at least partially attained by using a helical array of abrasive elements that has a high eccentric mass (e.g., the centers of mass of the abrasive elements are significantly offset from the central longitudinal axis of the drive shaft). Further, in some embodiments this feature can be at least partially attained by using multiple abrasive elements that are radially offset from each other around the drive shaft such that the centers of the abrasive elements are not coaxial with each other.

Fourth, in some embodiments rotational atherectomy systems described herein include user controls that are convenient and straight-forward to operate. In one such example, the user controls can include selectable elements that correspond to the diametric size of the implanted graft(s) to be treated. When the clinician-user selects the particular graft size, the system will determine an appropriate rpm of the drive shaft to obtain the desired orbit of the abrasive element(s) for the particular graft size. Hence, in such a case the clinician-user conveniently does not need to explicitly select or control the rpm of the drive shaft. In another example, the user controls can include selectable elements that correspond to the speed of drive shaft rotations. In some such examples, the user can conveniently select "low," "medium," or "high" speeds.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 shows an example user control unit of a rotational atherectomy system being operated by a clinician-user to perform a rotational atherectomy procedure above the knee of a patient.

FIG. 14 is a longitudinal cross-sectional view of a distal portion of an example rotational atherectomy device showing a multi-portion abrasive element and a distal stability element with an abrasive coating.

FIG. 15 is a side view of a distal portion of another example rotational atherectomy device showing a multi-portion abrasive element and a distal stability element with an abrasive coating. The individual portions of the multi-portion abrasive element are offset from each other around the drive shaft such that the centers of mass of the abrasive element portions define a spiral path around the drive shaft axis.

Like reference symbols in the various drawings indicate like elements.

DETAILED DESCRIPTION OF ILLUSTRATIVE EMBODIMENTS

Figure 1:
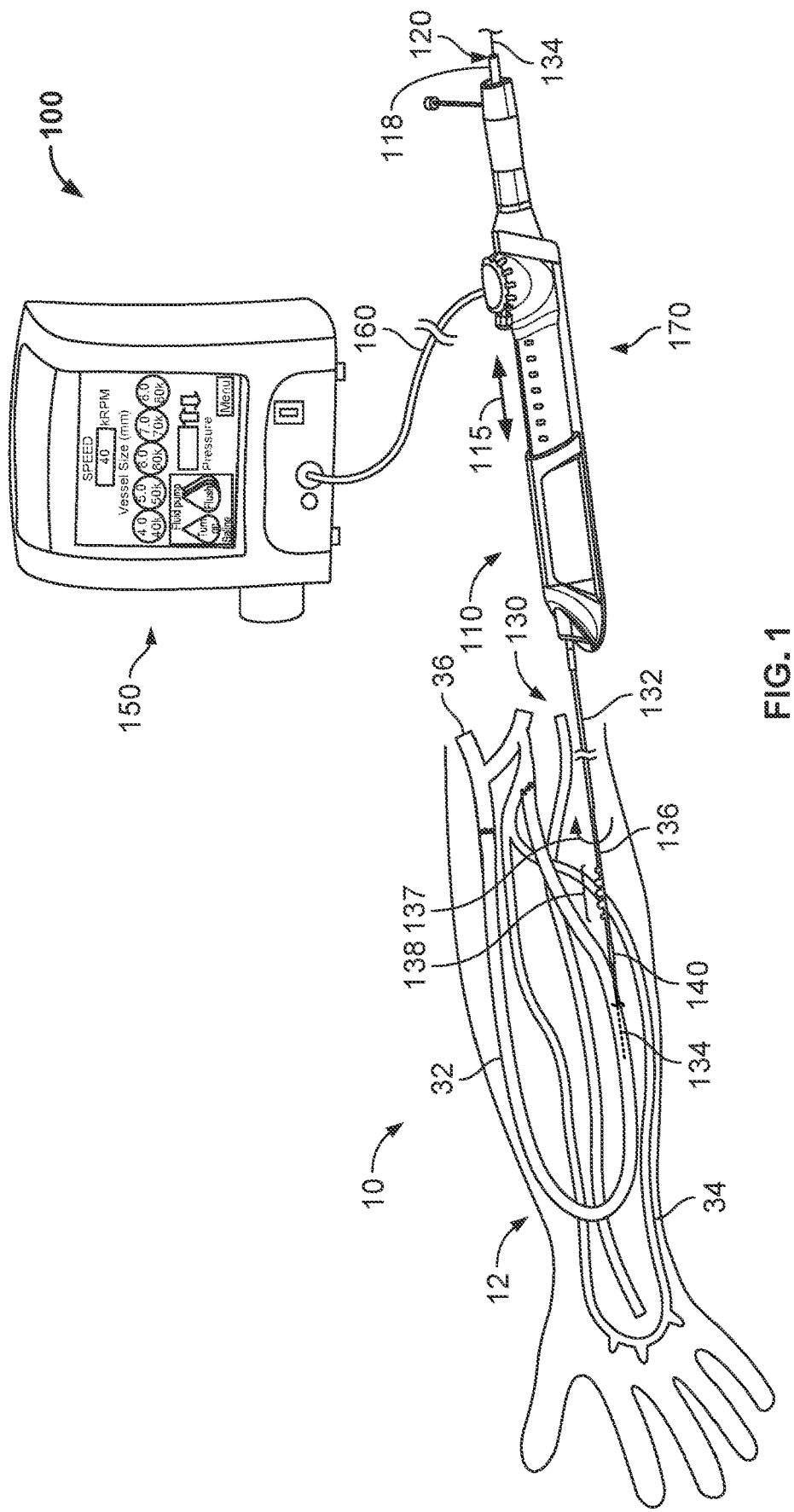
FIG. 1 shows an example rotational atherectomy system that is being used to perform a rotational atherectomy procedure in an arm of a patient.

Referring to FIG. 1, in some embodiments a rotational atherectomy system 100 for removing or reducing stenotic lesions in implanted grafts 32 (e.g., a synthetic AV graft) can include a rotational atherectomy device 170 and a controller 150. In some embodiments, the rotational atherectomy device 170 can include a guidewire 134, an actuator handle assembly 110, and an elongate flexible drive shaft assembly 130. The drive shaft assembly 130 extends distally from the handle assembly 110. The controller 150 can be connected to the handle assembly 110 via a cable assembly 160. The handle assembly 110 and controller 150 can be operated by a clinician to perform and control the rotational atherectomy procedure. In some embodiments, the actuator handle assembly 110 can be an electric handle that includes an electric motor, and can include speed controls, actuator buttons, and other functions to perform and control the rotational atherectomy procedure.

In the depicted embodiment, the elongate flexible drive shaft assembly 130 includes a sheath 132 and a flexible drive shaft 136. A proximal end of the sheath 132 is fixed to a distal end of the handle assembly 110. The flexible drive shaft 136 is slidably and rotatably disposed within a lumen of the sheath 132. The flexible drive shaft 136 defines a longitudinal lumen in which the guidewire 134 is slidably disposed. As depicted, the flexible drive shaft 136 includes a torque-transmitting coil that defines the longitudinal lumen along a central longitudinal axis, and the drive shaft 136 is configured to rotate about the longitudinal axis while the sheath 132 remains generally stationary. Hence, as described further below, during a rotational atherectomy procedure the flexible drive shaft 136 is in motion (e.g., rotating and longitudinally translating) while the sheath 132 and the guidewire 134 are generally stationary.

The rotational atherectomy device 170 can include one or more abrasive elements 138 that are eccentrically-fixed to the drive shaft 136 proximal of a distal stability element 140. In some embodiments, the distal stability element 140 is concentrically-fixed to the drive shaft 136 between the one or more abrasive elements 138 and a distal drive shaft extension portion. As such, the center of mass of the distal stability element 140 is aligned with the central axis of the drive shaft 136 while the center of mass of each abrasive element 138 is offset from the central axis of the drive shaft 136.

Still referring to FIG. 1, the graft 32 to be treated is in an arm 12 of a patient 10. For example, the graft 32 may be located below an elbow of the patient 10. In the depicted example, the graft 32 is a loop graft 32. In some embodiments, the distal portion of the rotational atherectomy device 170 is introduced into the vasculature by penetrating through a wall of the graft 32. In some embodiments, the graft 32 may be connecting a radial artery or a brachial artery 34 to a median cubital vein or a basilic vein 36. As shown in the depicted embodiment, the rotational atherectomy device 170 is inserted such that a distal portion of the rotational atherectomy device 170 is pointed toward a venous vessel, such as a median cubital or basilic vein 36. The abrasive elements 138 on the drive shaft 136 of the rotational atherectomy device 170 can be rotated to remove one or more lesions in the graft 32.

In some embodiments, the graft 32 is a self-healing graft, such that punctures in the graft caused by insertion of the rotational atherectomy device 170 will close and heal without additional aid. In some embodiments, the graft 32 can have an outer diameter of from about 4 millimeters (mm) to about 8 mm.

Figure 2:
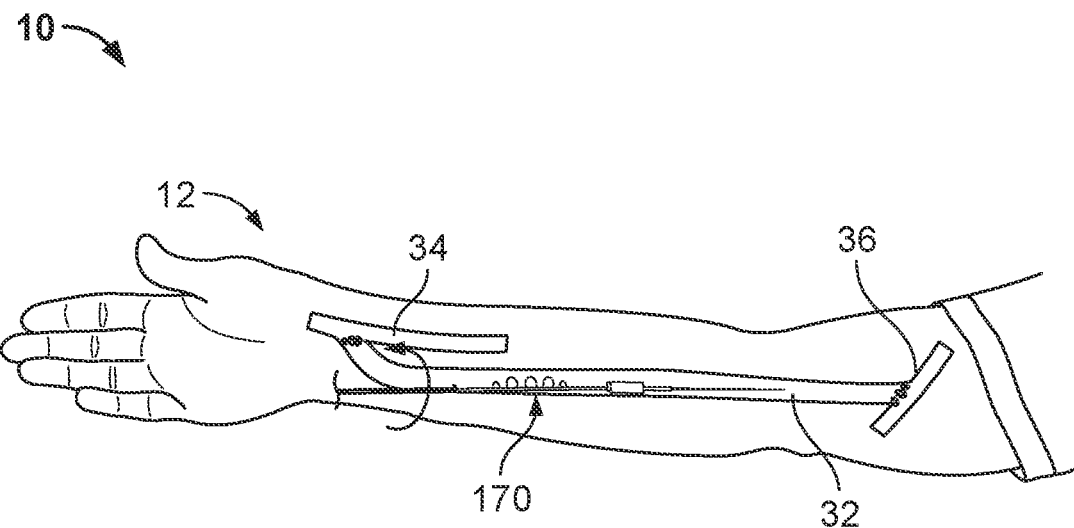
FIG. 2 shows the example rotational atherectomy device of FIG. 1 within a region of a lesion in a graft located in an arm of a patient.

Referring to FIG. 2, in another example, the graft 32 to be treated is in an arm 12 of a patient 10. For example, the graft 32 may be located below an elbow of the patient 10. In the depicted example, the graft 32 is a straight graft 32. In some embodiments, the graft 32 may be connecting a radial artery 34 to one of a median cubital vein, a basilic vein, or a cephalic vein 36. In some embodiments, the rotational atherectomy device 170 can be inserted such that a distal portion of the rotational atherectomy device 170 is pointed toward the median cubital vein, the basilic vein, or the cephalic vein 36. The abrasive elements on the rotational atherectomy device 170 can be rotated to remove a lesion in the graft 32.

Figure 3:
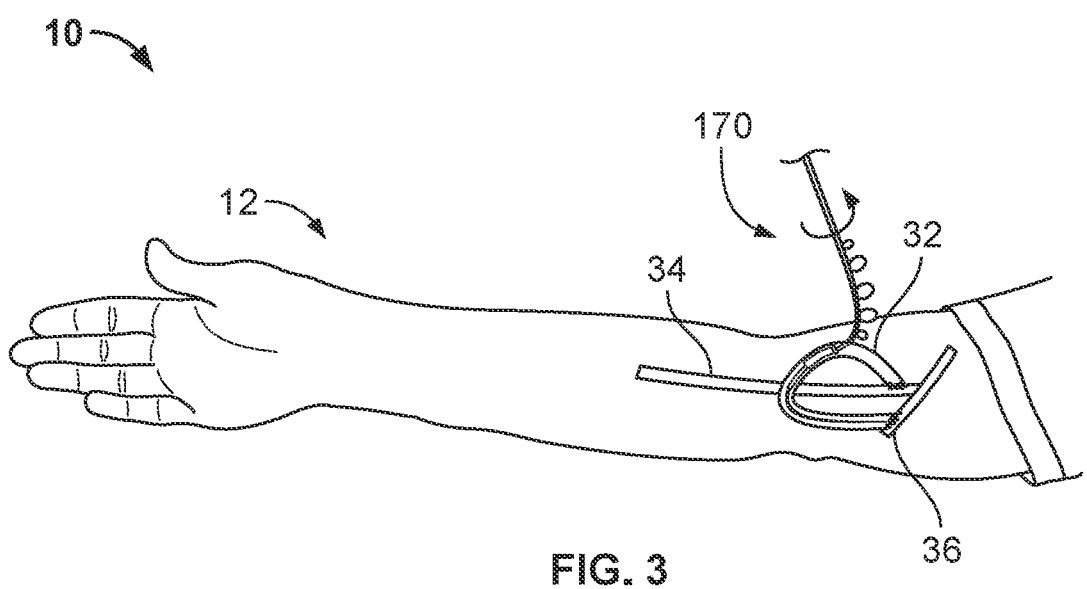
FIG. 3 shows the example rotational atherectomy device of FIG. 1 within a region of a lesion in a graft located in an arm of a patient.

Referring to FIG. 3, in some embodiments, the graft 32 to be treated is in an arm 12 of a patient 10. For example, the graft 32 may be located below an elbow of the patient 10. In some examples, the graft 32 is a loop graft 32. In some embodiments, the graft 32 may be connecting a radial artery or a brachial artery 34 to a median cubital vein or a basilic vein 36. In some embodiments, the rotational atherectomy device 170 can be inserted such that a distal portion of the rotational atherectomy device 170 is pointed toward the median cubital vein or the basilic vein 36. The abrasive elements on the rotational atherectomy device 170 can be rotated to remove a lesion in the graft 32.

Figure 4:
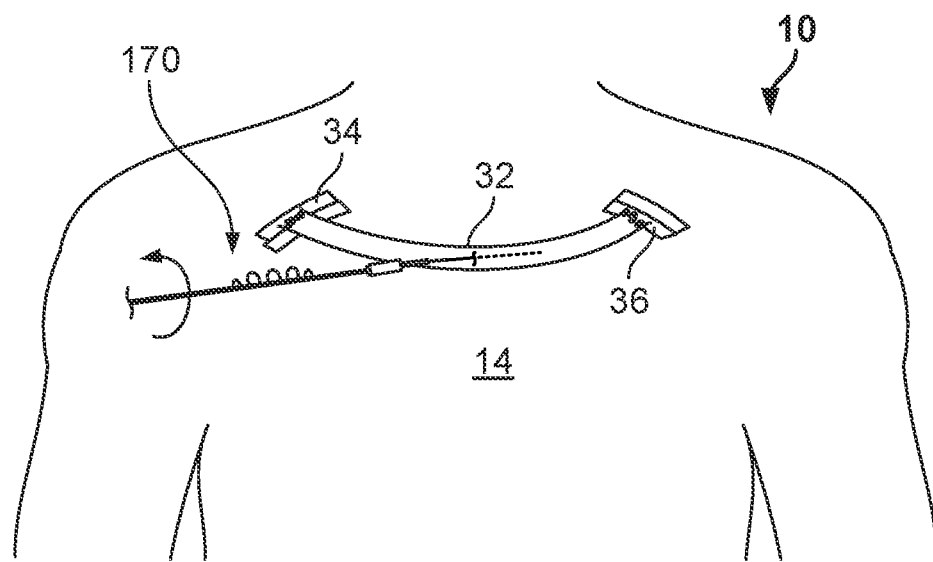
FIG. 4 shows the example rotational atherectomy device of FIG. 1 within a region of a lesion in a graft located in a chest of a patient.

Referring to FIG. 4, in some examples, the graft 32 to be treated is in a torso 14 of a patient 10. For example, the graft 32 may be located across a chest of the patient 10. In some embodiments, the graft 32 may be connecting an axillary artery 34 to an axillary vein 36. In the depicted embodiment, the rotational atherectomy device 170 can be inserted such that a distal portion of the rotational atherectomy device 170 is pointed toward the axillary vein 36. The abrasive elements on the rotational atherectomy device 170 can be rotated to remove a lesion in the graft 32.

Figure 5:
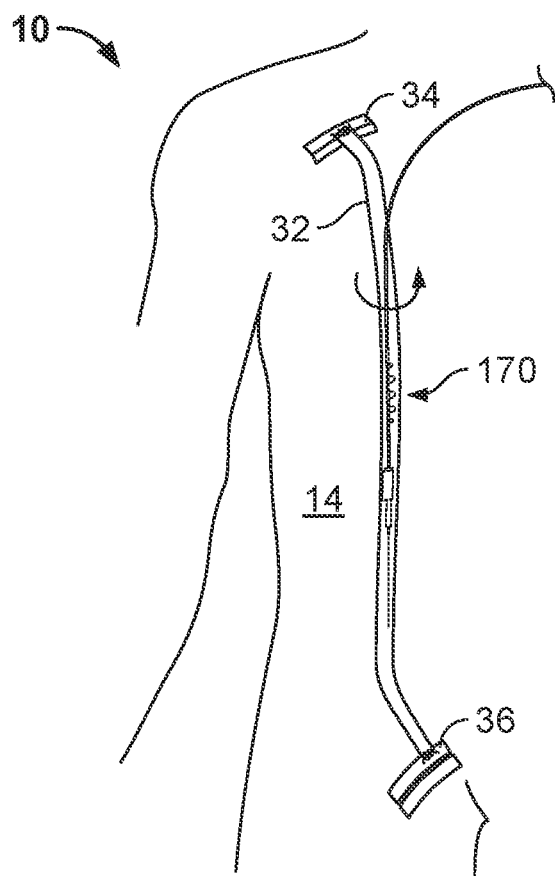
FIG. 5 shows the example rotational atherectomy device of FIG. 1 within a region of a lesion in a graft located in a torso of a patient.
Figure 7:
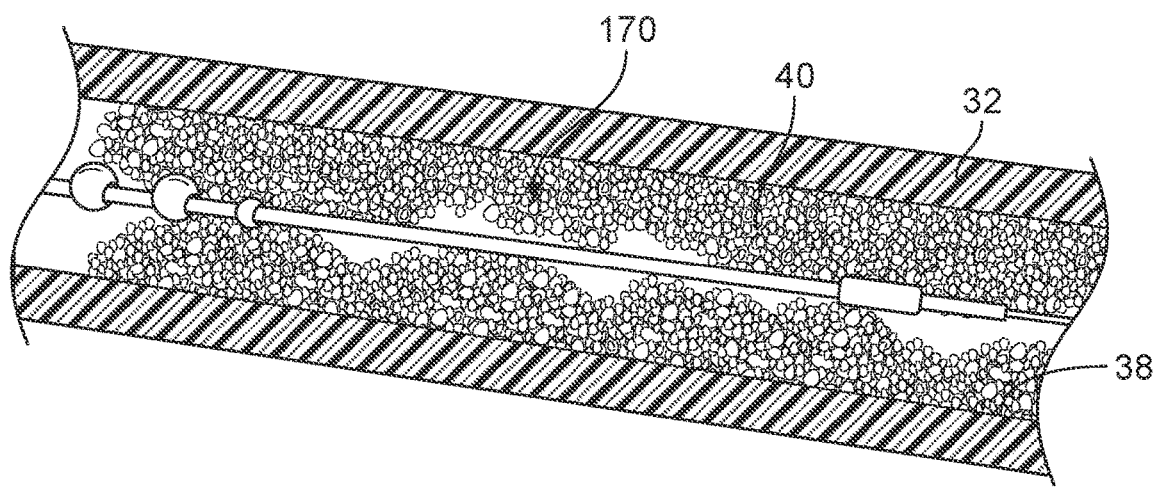
FIG. 7 shows the example rotational atherectomy device of FIG. 1 within in the region of the lesion.
Figure 8:
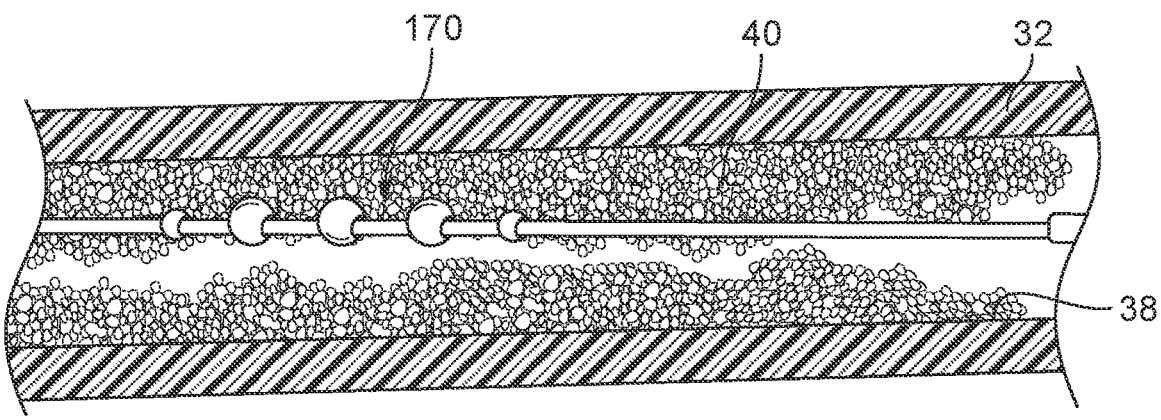
FIG. 8 shows the rotational atherectomy device of FIG. 1 with the abrasive element being rotated with a first diameter of orbit at a first longitudinal position.
Figure 9:
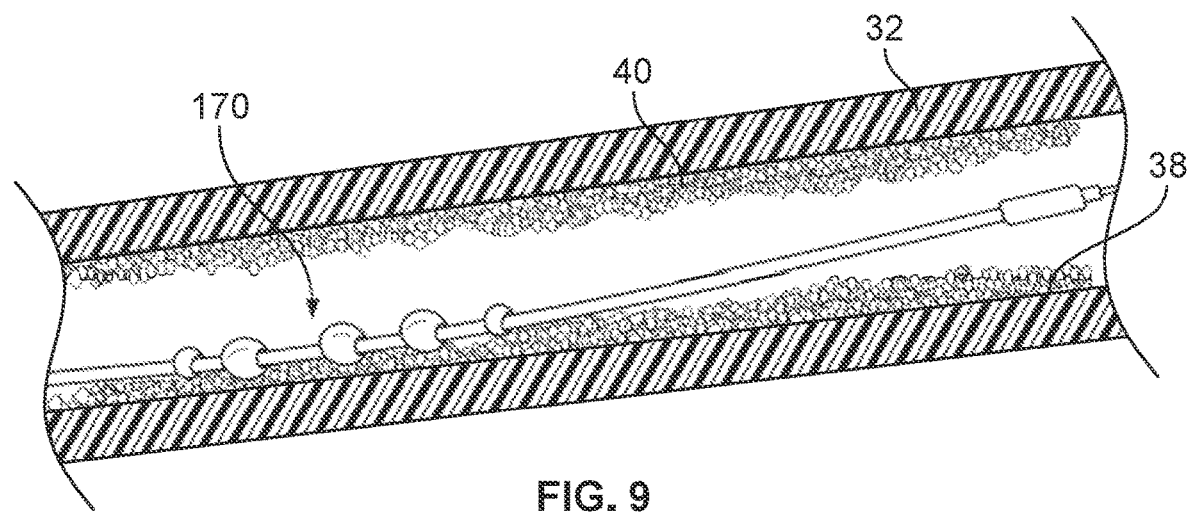
FIG. 9 shows the rotational atherectomy device of FIG. 1 with the abrasive element being rotated with a second diameter of orbit at the first longitudinal position.
Figure 10:
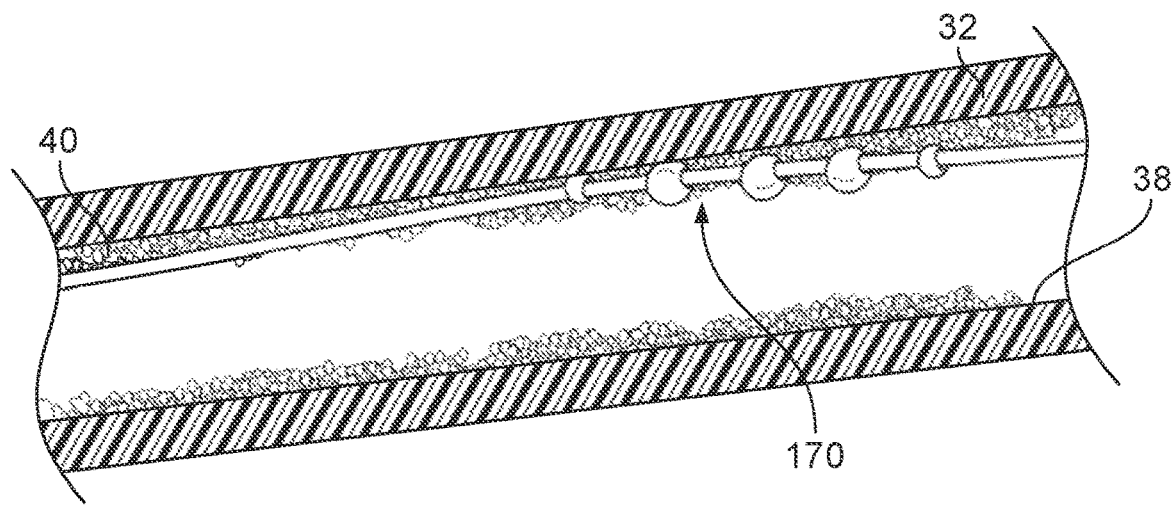
FIG. 10 shows the rotational atherectomy device of FIG. 1 with the abrasive element being rotated with the second diameter of orbit at a second longitudinal position.

Referring to FIG. 5, in some examples, the graft 32 to be treated is in a torso 14 of a patient 10. In some embodiments, the graft 32 may be connecting an axillary artery 34 to a saphenous vein 36 of the patient 10. In the depicted embodiment, the rotational atherectomy device 170 can be inserted such that a distal portion of the rotational atherectomy device 170 is pointed toward the saphenous vein 36. The abrasive elements on the rotational atherectomy device 170 can be rotated to remove a lesion in the graft 32.

Referring back to FIG. 1, in some optional embodiments, an inflatable member (not shown) can surround a distal end portion of the sheath 132. Such an inflatable member can be selectively expandable between a deflated low-profile configuration and an inflated deployed configuration. The sheath 132 may define an inflation lumen through which the inflation fluid can pass (to and from the optional inflatable member).

The inflatable member can be in the deflated low-profile configuration during the navigation of the drive shaft assembly 130 through the patient's graft to a target location. Then, at the target location, the inflatable member can be inflated so that the outer diameter of the inflatable member contacts the wall of the vessel. In that arrangement, the inflatable member advantageously stabilizes the drive shaft assembly 130 in the vessel during the rotational atherectomy procedure.

Still referring to FIG. 1, the flexible drive shaft 136 is slidably and rotatably disposed within a lumen of the sheath 132. A distal end portion of the drive shaft 136 extends distally of the distal end of the sheath 132 such that the distal end portion of the drive shaft 136 is exposed (e.g., not within the sheath 132, at least not during the performance of the actual rotational atherectomy).

In the depicted embodiment, the exposed distal end portion of the drive shaft 136 includes one or more abrasive elements 138, a (optional) distal stability element 140, and a distal drive shaft extension portion 142. In the depicted embodiment, the one or more abrasive elements 138 are eccentrically-fixed to the drive shaft 136 proximal of the distal stability element 140. In this embodiment, the distal stability element 140 is concentrically-fixed to the drive shaft 136 between the one or more abrasive elements 138 and the distal drive shaft extension portion 142. As such, the center of mass of the distal stability element 140 is aligned with the central axis of the drive shaft 136 while the center of mass of each abrasive element 138 is offset from the central axis of the drive shaft 136. The distal drive shaft extension portion 142, which includes the torque-transmitting coil, is configured to rotate about the longitudinal axis extends distally from the distal stability element 140 and terminates at a free end of the drive shaft 136.

In some optional embodiments, a proximal stability element (not shown) is included. The proximal stability element can be constructed and configured similarly to the depicted embodiment of the distal stability element 140 (e.g., a metallic cylinder directly coupled to the torque-transmitting coil of the drive shaft 136 and concentric with the longitudinal axis of the drive shaft 136) while being located proximal to the one or more abrasive elements 138.

In the depicted embodiment, the distal stability element 140 has a center of mass that is axially aligned with a central longitudinal axis of the drive shaft 136, while the one or more abrasive elements 138 (collectively and/or individually) have a center of mass that is axially offset from central longitudinal axis of the drive shaft 136. Accordingly, as the drive shaft 136 is rotated about its longitudinal axis, the principle of centrifugal force will cause the one or more abrasive elements 138 (and the portion of the drive shaft 136 to which the one or more abrasive elements 138 are affixed) to follow a transverse generally circular orbit (e.g., somewhat similar to a "jump rope" orbital movement) relative to the central axis of the drive shaft 136 (as described below, for example, in connection with FIGS. 11-13). In general, faster speeds (rpm) of rotation of the drive shaft 136 will result in larger diameters of the orbit (within the limits of the graft diameter). The orbiting one or more abrasive elements 138 will contact the stenotic lesion to ablate or abrade the lesion to a reduced size (i.e., small particles of the lesion will be abraded from the lesion).

The rotating distal stability element 140 will remain generally at the longitudinal axis of the drive shaft 136 as the drive shaft 136 is rotated (as described below, for example, in connection with FIGS. 11-13). In some optional embodiments, two or more distal stability elements 140 are included. As described further below, contemporaneous with the rotation of the drive shaft 136, the drive shaft 136 can be translated back and forth along the longitudinal axis of the drive shaft 136. Hence, lesions can be abraded radially and longitudinally by virtue of the orbital rotation and translation of the one or more abrasive elements 138, respectively.

The flexible drive shaft 136 of rotational atherectomy system 100 is laterally flexible so that the drive shaft 136 can readily conform to the non-linear grafts of the patient, and so that a portion of the drive shaft 136 at and adjacent to the one or more abrasive elements 138 will laterally deflect when acted on by the centrifugal forces resulting from the rotation of the one or more eccentric abrasive elements 138. In this embodiment, the drive shaft 136 comprises one or more helically wound wires (or filars) that provide one or more torque-transmitting coils of the drive shaft 136 (as described below, for example, in connection with FIGS. 14-15). In some embodiments, the one or more helically wound wires are made of a metallic material such as, but not limited to, stainless steel (e.g., 316, 316L, or 316LVM), nitinol, titanium, titanium alloys (e.g., titanium beta 3), carbon steel, or another suitable metal or metal alloy. In some alternative embodiments, the filars are or include graphite, Kevlar, or a polymeric material. In some embodiments, the filars can be woven, rather than wound. In some embodiments, individual filars can comprise multiple strands of material that are twisted, woven, or otherwise coupled together to form a filar. In some embodiments, the filars have different cross-sectional geometries (size or shape) at different portions along the axial length of the drive shaft 136. In some embodiments, the filars have a cross-sectional geometry other than a circle, e.g., an ovular, square, triangular, or another suitable shape.

In this embodiment, the drive shaft 136 has a hollow core. That is, the drive shaft 136 defines a central longitudinal lumen running therethrough. The lumen can be used to slidably receive the guidewire 134 therein, as will be described further below. In some embodiments, the lumen can be used to aspirate particulate or to convey fluids that are beneficial for the atherectomy procedure.

In some embodiments, the drive shaft 136 includes an optional coating on one or more portions of the outer diameter of the drive shaft 136. The coating may also be described as a jacket, a sleeve, a covering, a casing, and the like. In some embodiments, the coating adds column strength to the drive shaft 136 to facilitate a greater ability to push the drive shaft 136 through stenotic lesions. In addition, the coating can enhance the rotational stability of the drive shaft 136 during use. In some embodiments, the coating is a flexible polymer coating that surrounds an outer diameter of the coil (but not the abrasive elements 138 or the distal stability element 140) along at least a portion of drive shaft 136 (e.g., the distal portion of the drive shaft 136 exposed outwardly from the sheath 132). In some embodiments, a portion of the drive shaft 136 or all of the drive shaft 136 is uncoated. In particular embodiments, the coating is a fluid impermeable material such that the lumen of the drive shaft 136 provides a fluid impermeable flow path along at least the coated portions of the drive shaft 136.

The coating may be made of materials including, but not limited to, PEBEX, PICOFLEX, PTFE, ePTFE, FEP, PEEK, silicone, PVC, urethane, polyethylene, polypropylene, and the like, and combinations thereof. In some embodiments, the coating covers the distal stability element 140 and the distal extension portion 142, thereby leaving only the one or more abrasive elements 138 exposed (non-coated) along the distal portion of the drive shaft 136. In alternative embodiments, the distal stability element 140 is not covered with the coating, and thus would be exposed like the abrasive elements 138. In some embodiments, two or more layers of the coating can be included on portions of the drive shaft 136. Further, in some embodiments different coating materials (e.g., with different durometers and/or stiffnesses) can be used at different locations on the drive shaft 136.

In the depicted embodiment, the distal stability element 140 is a metallic cylindrical member having an inner diameter that surrounds a portion of the outer diameter of the drive shaft 136. In some embodiments, the distal stability element 140 has a longitudinal length that is greater than a maximum exterior diameter of the distal stability element 140. In the depicted embodiment, the distal stability element 140 is coaxial with the longitudinal axis of the drive shaft 136. Therefore, the center of mass of the distal stability element 140 is axially aligned (non-eccentric) with the longitudinal axis of the drive shaft 136. In alternative rotational atherectomy device embodiments, stability element(s) that have centers of mass that are eccentric in relation to the longitudinal axis may be included in addition to, or as an alternative to, the coaxial stability elements 140. For example, in some alternative embodiments, the stability element(s) can have centers of mass that are eccentric in relation to the longitudinal axis and that are offset 180 degrees (or otherwise oriented) in relation to the center of mass of the one or more abrasive elements 138.

The distal stability element 140 may be made of a suitable biocompatible material, such as a higher-density biocompatible material. For example, in some embodiments the distal stability element 140 may be made of metallic materials such as stainless steel, tungsten, molybdenum, iridium, cobalt, cadmium, and the like, and alloys thereof. The distal stability element 140 has a fixed outer diameter. That is, the distal stability element 140 is not an expandable member in the depicted embodiment. The distal stability element 140 may be mounted to the filars of the drive shaft 136 using a biocompatible adhesive, by welding, by press fitting, and the like, and by combinations thereof. The coating may also be used in some embodiments to attach or to supplement the attachment of the distal stability element 140 to the filars of the drive shaft 136. Alternatively, the distal stability element 140 can be integrally formed as a unitary structure with the filars of the drive shaft 136 (e.g., using filars of a different size or density, using filars that are double-wound to provide multiple filar layers, or the like). The maximum outer diameter of the distal stability element 140 may be smaller than the maximum outer diameters of the one or more abrasive elements 138.

In some embodiments, the distal stability element 140 has an abrasive coating on its exterior surface. For example, in some embodiments a diamond coating (or other suitable type of abrasive coating) is disposed on the outer surface of the distal stability element 140. In some cases, such an abrasive surface on the distal stability element 140 can help facilitate the passage of the distal stability element 140 through vessel restrictions (such as calcified areas of a blood vessel).

In some embodiments, the distal stability element 140 has an exterior cylindrical surface that is smoother and different from an abrasive exterior surface of the one or more abrasive elements 138. That may be the case whether or not the distal stability element 140 have an abrasive coating on its exterior surface. In some embodiments, the abrasive coating on the exterior surface of the distal stability element 140 is rougher than the abrasive surfaces on the one or more abrasive elements 138.

Still referring to FIG. 1, the one or more abrasive elements 138 (which may also be referred to as a burr, multiple burrs, or (optionally) a helical array of burrs) can comprise a biocompatible material that is coated with an abrasive media such as diamond grit, diamond particles, silicon carbide, and the like. In the depicted embodiment, the abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating, such as a diamond grit coating.

In the depicted embodiment, the two outermost abrasive elements are smaller in maximum diameter than the three inner abrasive elements. In some embodiments, all of the abrasive elements are the same size. In particular embodiments, three or more different sizes of abrasive elements are included. Any and all such possible arrangements of sizes of abrasive elements are envisioned and within the scope of this disclosure.

Also, in the depicted embodiment, the center of mass of each abrasive element 138 is offset from the longitudinal axis of the drive shaft 136. Therefore, as the eccentric one or more abrasive elements 138 are rotated (along an orbital path), at least a portion of the abrasive surface of the one or more abrasive elements 138 can make contact with surrounding stenotic lesion material. As with the distal stability element 140, the eccentric one or more abrasive elements 138 may be mounted to the filars of the torque-transmitting coil of the drive shaft 136 using a biocompatible adhesive, high temperature solder, welding, press fitting, and the like. In some embodiments, a hypotube is crimped onto the drive shaft and an abrasive element is laser welded to the hypotube. Alternatively, the one or more abrasive elements 138 can be integrally formed as a unitary structure with the filars of the drive shaft 136 (e.g., using filars that are wound in a different pattern to create an axially offset structure, or the like).

In some embodiments, the spacing of the distal stability element 140 relative to the one or more abrasive elements 138 and the length of the distal extension portion 142 can be selected to advantageously provide a stable and predictable rotary motion profile during high-speed rotation of the drive shaft 136. For example, in embodiments that include the distal drive shaft extension portion 142, the ratio of the length of the distal drive shaft extension 142 to the distance between the centers of the one or more abrasive elements 138 and the distal stability element 140 is about 1:0.5, about 1:0.8, about 1:1, about 1.1:1, about 1.2:1, about 1.5:1, about 2:1, about 2.5:1, about 3:1, or higher than 3:1.

Still referring to FIG. 1, the rotational atherectomy system 100 also includes the actuator handle assembly 110. The actuator handle assembly 110 includes a housing and a carriage assembly. The carriage assembly is slidably translatable along the longitudinal axis of the handle assembly 110 as indicated by the arrow 115. For example, in some embodiments the carriage assembly can be translated, without limitation, about 8 cm to about 12 cm, or about 6 cm to about 10 cm, or about 4 cm to about 8 cm, or about 6 cm to about 14 cm. As the carriage assembly is translated in relation to the housing, the drive shaft 136 translates in relation to the sheath 132 in a corresponding manner.

In the depicted embodiment, the carriage assembly includes a valve actuator. In some embodiments, an electric motor for driving rotations of the drive shaft 136 is coupled to the carriage assembly such that the valve actuator is an electrical switch instead. In the depicted embodiment, the valve actuator is a button that can be depressed to actuate a compressed gas control valve (on/off; defaulting to off) mounted to the carriage assembly. While the valve actuator is depressed, a compressed gas (e.g., air, nitrogen, etc.) is supplied through the valve to a turbine member that is rotatably coupled to the carriage assembly and fixedly coupled to the drive shaft 136. Hence, an activation of the valve actuator will result in a rotation of the turbine member and, in turn, the drive shaft 136 (as depicted by arrow 137). In some embodiments, the rotational atherectomy system 100 is configured to rotate the drive shaft 136 at a high speed of rotation (e.g., 20,000-160,000 rpm) such that the eccentric one or more abrasive elements 138 revolve in an orbital path to thereby contact and remove portions of a target lesion (even those portions of the lesion that are spaced farther from the axis of the drive shaft 136 than the maximum radius of the one or more abrasive elements 138).

To operate the handle assembly 110 during a rotational atherectomy procedure, a clinician can grasp the carriage assembly and depress the valve actuator with the same hand. The clinician can move (translate) the carriage assembly distally and proximally by hand (e.g., back and forth in relation to the housing), while maintaining the valve actuator in the depressed state. In that manner, a target lesion(s) can be ablated radially and longitudinally by virtue of the resulting orbital rotation and translation of the one or more abrasive elements 138, respectively.

During an atherectomy treatment, in some cases the guidewire 134 is left in position in relation to the drive shaft 136 generally as shown. For example, in some cases the portion of the guidewire 134 that is extending beyond the distal end of the drive shaft 136 (or extension portion 142) is about 4 inches to about 8 inches (about 10 cm to about 20 cm), about 8 inches to about 12 inches (about 20 cm to about 30 cm), about 4 inches to about 16 inches (about 10 cm to about 40 cm), or about 2 inches to about 20 inches (about 5 cm to about 50 cm). In some cases, the guidewire 134 is pulled back to be within (while not extending distally from) the drive shaft 136 during an atherectomy treatment. The distal end of the guidewire 134 may be positioned anywhere within the drive shaft 136 during an atherectomy treatment. In some cases, the guidewire 134 may be completely removed from within the drive shaft during an atherectomy treatment. The extent to which the guidewire 134 is engaged with the drive shaft 136 during an atherectomy treatment may affect the size of the orbital path of the one or more abrasive elements 138.

In the depicted embodiment, the handle assembly 110 also includes a guidewire detention mechanism 118. The guidewire detention mechanism 118 can be selectively actuated (e.g., rotated) to releasably clamp and maintain the guidewire 134 in a stationary position relative to the handle assembly 110 (and, in turn, stationary in relation to rotations of the drive shaft 136 during an atherectomy treatment). While the drive shaft 136 and handle assembly 110 are being advanced over the guidewire 134 to put the one or more abrasive elements 138 into a targeted position within a patient's graft 32, the guidewire detention mechanism 118 will be unactuated so that the handle assembly 110 is free to slide in relation to the guidewire 134. Then, when the clinician is ready to begin the atherectomy treatment, the guidewire detention mechanism 118 can be actuated to releasably detain/lock the guidewire 134 in relation to the handle assembly 110. That way the guidewire 134 will not rotate while the drive shaft 136 is rotating, and the guidewire 134 will not translate while the carriage assembly is being manually translated.

Still referring to FIG. 1, the rotational atherectomy system 100 also includes the controller 150. In the depicted embodiment, the controller 150 includes a user interface that includes a plurality of selectable inputs that correspond to a plurality of vessel sizes (diameters). To operate the rotational atherectomy system 100, the user can select a particular one of the selectable inputs that corresponds to the diameter of the vessel being treated. In response, the controller 150 will determine the appropriate gas pressure for rotating the drive shaft 136 in a vessel of the selected diameter (faster rpm for larger vessels and slower rpm for smaller vessel), and supply the gas at the appropriate pressure to the handle assembly 110.

In some embodiments, the controller 150 is pole-mounted. The controller 150 can be used to control particular operations of the handle assembly 110 and the drive shaft assembly 130. For example, the controller 150 can be used to compute, display, and adjust the rotational speed of the drive shaft 136.

In some embodiments, the controller 150 can include electronic controls that are in electrical communication with a turbine RPM sensor located on the carriage assembly. The controller 150 can convert the signal(s) from the sensor into a corresponding RPM quantity and display the RPM on the user interface. If a speed adjustment is desired, the clinician can increase or decrease the rotational speed of the drive shaft 136. In result, a flow or pressure of compressed gas supplied from the controller 150 to the handle assembly 110 (via the cable assembly 160) will be modulated. The modulation of the flow or pressure of the compressed gas will result in a corresponding modulation of the RPM of the turbine member and of the drive shaft 136.

In some embodiments, the controller 150 includes one or more interlock features that can enhance the functionality of the rotational atherectomy system 100. In one such example, if the controller 150 does not detect any electrical signal (or a proper signal) from the turbine RPM sensor, the controller 150 can discontinue the supply of compressed gas. In another example, if a pressure of a flush liquid supplied to the sheath 132 is below a threshold pressure value, the controller 150 can discontinue the supply of compressed gas.

Still referring to FIG. 1, the rotational atherectomy system 100 can include an electric handle with an electric motor. In some embodiments, the electric handle can include a user interface that includes a plurality of selectable inputs that correspond to a plurality of vessel sizes (diameters). To operate the rotational atherectomy system 100, the user can select a particular one of the selectable inputs that corresponds to the diameter of the vessel being treated. In response, the electric handle will determine the appropriate rpm for rotating the drive shaft 136 in a vessel of the selected diameter (faster rpm for larger vessels and slower rpm for smaller vessel), and operate the electric motor accordingly.

Referring to FIG. 6, the rotational atherectomy system 100 also includes the controller 150. In the depicted embodiment, the controller 150 includes a user interface that includes a plurality of selectable inputs that correspond to a plurality of graft sizes (diameters). Other types of user interfaces are also envisioned. To operate the rotational atherectomy system 100, the user can select a particular one of the selectable inputs that corresponds to the diameter of the graft being treated. In response, the controller 150 will determine the appropriate gas pressure for rotating the one or more abrasive elements 138 in a graft of the selected diameter (faster RPM for larger grafts and slower RPM for smaller grafts), and supply the gas at the appropriate pressure to the handle assembly 110. In some embodiments, the driver for rotation of the one or more abrasive elements 138 is an electrical motor rather than the pneumatic motor included in the depicted example. In the depicted example, the graft 32 to be treated is in a leg 16 of a patient. In particular, the graft 32 is above a knee (e.g., between a femoral artery and a saphenous vein, without limitation).

In some embodiments, the user interface is configured such that the user can simply select either "LOW," "MED," or "HIGH" speed via the selectable inputs. Based on the user's selection of either "LOW," "MED," or "HIGH," the controller 150 will provide a corresponding output for rotating the drive shaft at a corresponding rotational speed. It should be understood that the user interfaces are merely exemplary and non-limiting. That is, other types of user interface controls can also be suitably used, and are envisioned within the scope of this disclosure.

Referring to FIGS. 7-13, the rotational atherectomy system 100 can be used to treat a graft 32 having a stenotic lesion 40 along an inner wall 38 of the graft 32. The rotational atherectomy system 100 is used to fully or partially remove the stenotic lesion 40, thereby removing or reducing the blockage within the graft 32 caused by the stenotic lesion 40. By performing such a treatment, the blood flow through the graft 32 may be thereafter increased or otherwise improved. The graft 32 and lesion 40 are shown in longitudinal cross-sectional views to enable visualization of the rotational atherectomy system 100.

Briefly, in some implementations the following activities may occur to achieve the deployed arrangement shown in FIGS. 7-13. In some embodiments, an introducer sheath (not shown) can be percutaneously advanced into the vasculature of the patient. The guidewire 134 can then be inserted through a lumen of the introducer sheath and navigated within the patient's graft 32 to a target location (e.g., the location of the lesion 40). Techniques such as x-ray fluoroscopy or ultrasonic imaging may be used to provide visualization of the guidewire 134 and other atherectomy system components during placement. In some embodiments, no introducer sheath is used and the guidewire 134 is inserted without assistance from a sheath.

Next, portions of the rotational atherectomy system 100 can be inserted over the guidewire 134. For example, an opening to the lumen of the drive shaft 136 at the distal free end of the drive shaft 136 (e.g., at the distal end of the optional distal drive shaft extension portion 142) can be placed onto the guidewire 134, and then the drive shaft assembly 130 and handle assembly 110 can be gradually advanced over the guidewire 134 to the position in relation to the lesion 40. In some cases, the drive shaft 136 is disposed fully within the lumen of the sheath 132 during the advancing. In some cases, a distal end portion of the drive shaft 136 extends from the distal end opening 143 of the sheath 132 during the advancing. Eventually, after enough advancing, the proximal end of the guidewire 134 will extend proximally from the handle assembly 110 (via the access port 120 defined by the handle housing).

In some cases (such as in the depicted example), the lesion 40 may be so large (i.e., so extensively occluding the vessel 10) that it is difficult or impossible to push the distal stability element 140 through the lesion 40. In some such cases, an abrasive outer surface on the distal stability element 140 can be used to help facilitate passage of the distal stability element 140 into or through the lesion 40. In some such cases, the drive shaft 136 can be rotated to further help facilitate the distal stability element 140 to bore into/through the lesion 40.

Figure 11:
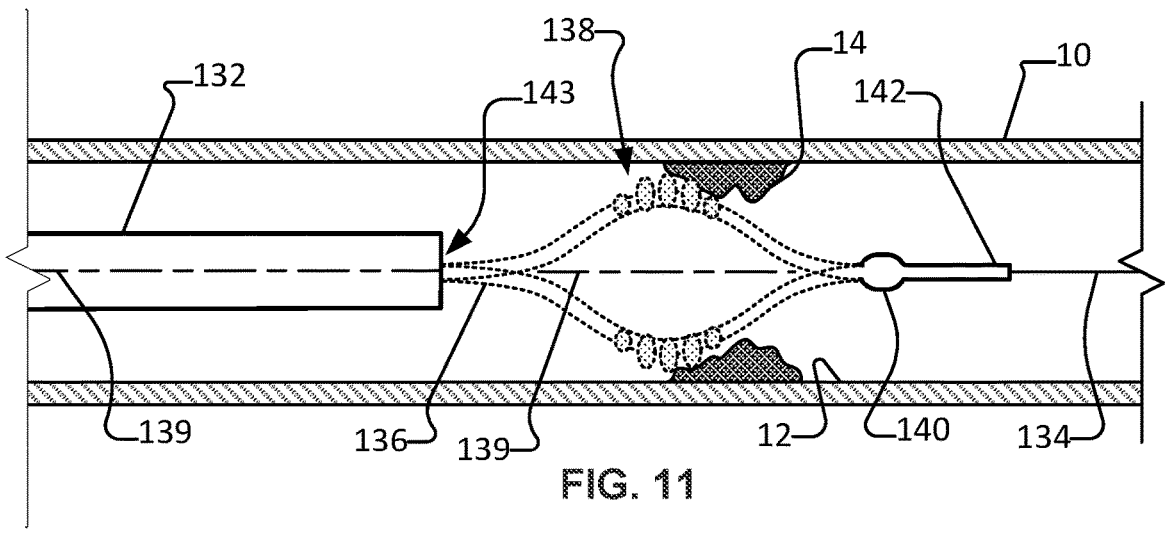
FIG. 11 shows the example rotational atherectomy device of FIG. 1 in use at a first longitudinal position in the region of the lesion. A multi-portion abrasive element of the rotational atherectomy device is being rotated along an orbital path to abrade the lesion.
Figure 12:
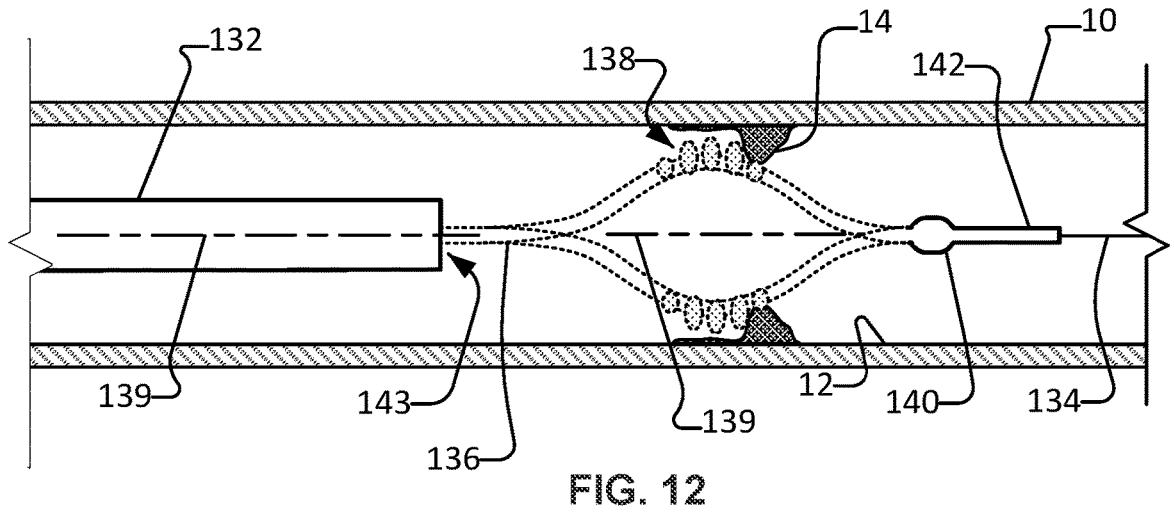
FIG. 12 shows the rotational atherectomy device of FIG. 1 with the abrasive element being rotated at a second longitudinal position that is distal of the first longitudinal position.
Figure 13:
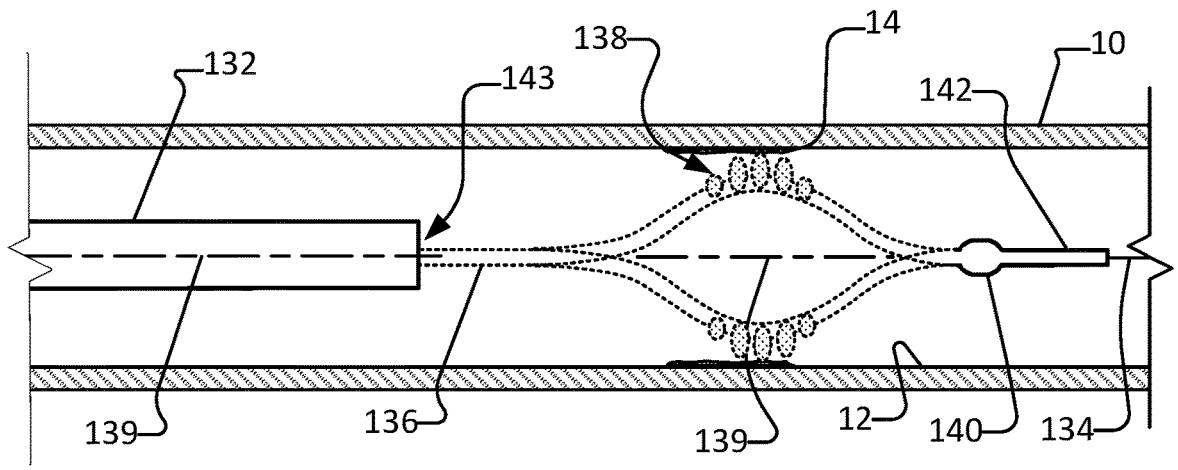
FIG. 13 shows the rotational atherectomy device of FIG. 1 with the abrasive element being rotated at a third longitudinal position that is distal of the second longitudinal position.
Figure 18:
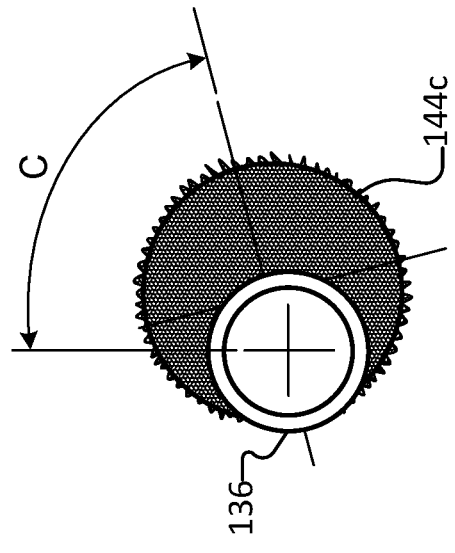
FIG. 18 is a transverse cross-sectional view of the rotational atherectomy device of FIG. 15 taken along the cutting-plane line 18-18.
Figure 17:
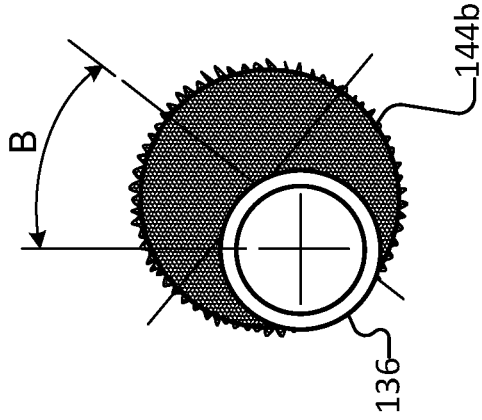
FIG. 17 is a transverse cross-sectional view of the rotational atherectomy device of FIG. 15 taken along the cutting-plane line 17-17.

Next, as depicted by FIGS. 11-13, the rotation and translational motions of the drive shaft 136 (and the one or more abrasive elements 138) can be commenced to perform ablation of the lesion 40.

In some implementations, prior to the ablation of the lesion 40 by the one or more abrasive elements 138, an inflatable member can be used as an angioplasty balloon to treat the lesion 40. That is, an inflatable member (on the sheath 132, for example) can be positioned within the lesion 40 and then inflated to compress the lesion 40 against the inner wall 38 of the graft 32. Thereafter, the rotational atherectomy procedure can be performed. In some implementations, such an inflatable member can be used as an angioplasty balloon after the rotational atherectomy procedure is performed. In some implementations, additionally or alternatively, a stent can be placed at lesion 40 using an inflatable member on the sheath 132 (or another balloon member associated with the drive shaft assembly 130) after the rotational atherectomy procedure is performed.

The guidewire 134 may remain extending from the distal end of the drive shaft 136 during the atherectomy procedure as shown. For example, as depicted by FIGS. 11-13, the guidewire 134 extends through the lumen of the drive shaft 136 and further extends distally of the distal end of the distal extension portion 142 during the rotation and translational motions of the drive shaft 136 (refer, for example, to FIGS. 11-13). In some alternative implementations, the guidewire 134 is withdrawn completely out of the lumen of the drive shaft 136 prior to during the rotation and translational motions of the drive shaft 136 for abrading the lesion 40. In other implementations, the guidewire 134 is withdrawn only partially. That is, in some implementations a portion of the guidewire 134 remains within the lumen of the drive shaft 136 during rotation of the drive shaft 136, but remains only in a proximal portion that is not subject to the significant orbital path in the area of the one or more abrasive elements 138 (e.g., remains within the portion of the drive shaft 136 that remains in the sheath 132).

To perform the atherectomy procedure, the drive shaft 136 is rotated at a high rate of rotation (e.g., 20,000-160,000 rpm) such that the eccentric one or more abrasive elements 138 revolve in an orbital path about an axis of rotation and thereby contacts and removes portions of the lesion 40.

Still referring to FIGS. 11-13, the rotational atherectomy system 100 is depicted during the high-speed rotation of the drive shaft 136. The centrifugal force acting on the eccentrically weighted one or more abrasive elements 138 causes the one or more abrasive elements 138 to orbit in an orbital path around the axis of rotation 139. In some implementations, the orbital path can be somewhat similar to the orbital motion of a "jump rope." As shown, some portions of the drive shaft 136 (e.g., a portion that is just distal of the sheath 132 and another portion that is distal of the distal stability element 140) can remain in general alignment with the axis of rotation 139, but the particular portion of the drive shaft 136 adjacent to the one or more abrasive elements 138 is not aligned with the axis of rotation 139 (and instead orbits around the axis 139). As such, in some implementations, the axis of rotation 139 may be aligned with the longitudinal axis of a proximal part of the drive shaft 136 (e.g., a part within the distal end of the sheath 132) and with the longitudinal axis of the distal extension portion 142 of the drive shaft 136.

In some implementations, as the one or more abrasive elements 138 rotates, the clinician operator slowly advances the carriage assembly distally (and, optionally, reciprocates both distally and proximally) in a longitudinal translation direction so that the abrasive surface of the one or more abrasive elements 138 scrapes against additional portions of the occluding lesion 40 to reduce the size of the occlusion, and to thereby improve the blood flow through the graft 32. This combination of rotational and translational motion of the one or more abrasive elements 138 is depicted by the sequence of FIGS. 11-13.

In some embodiments, the sheath 132 may define one or more lumens (e.g., the same lumen as, or another lumen than, the lumen in which the drive shaft 136 is located) that can be used for aspiration (e.g., of abraded particles of the lesion 40). In some cases, such lumens can be additionally or alternatively used to deliver perfusion and/or therapeutic substances to the location of the lesion 40, or to prevent backflow of blood from graft 32 into sheath 132.

Referring to FIG. 14, a distal end portion of the drive shaft 136 is shown in a longitudinal cross-sectional view. The distal end portion of the drive shaft 136 includes the one or more abrasive elements 138 that are eccentrically-fixed to the drive shaft 136, the distal stability element 140 with an abrasive outer surface, and the distal drive shaft extension portion 142.

In the depicted embodiment, the one or more abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating.

In the depicted embodiment, the two outermost abrasive elements of the abrasive elements 138 are smaller in maximum diameter than the three inner abrasive elements of the abrasive elements 138. In some embodiments, all of the abrasive elements are the same size. In particular embodiments, three or more different sizes of abrasive elements 138 are included. Any and all such possible arrangements of sizes of abrasive elements 138 are envisioned and within the scope of this disclosure.

The one or more abrasive elements 138 can be made to any suitable size. For clarity, the size of the one or more abrasive elements 138 will refer herein to the maximum outer diameter of individual abrasive elements of the one or more abrasive elements 138. In some embodiments, the one or more abrasive elements 138 are about 2 mm in size (maximum outer diameter). In some embodiments, the size of the one or more abrasive elements 138 is in a range of about 1.5 mm to about 2.5 mm, or about 1.0 mm to about 3.0 mm, or about 0.5 mm to about 4.0 mm, without limitation. Again, in a single embodiment, one or more of the abrasive elements 138 can have a different size in comparison to the other abrasive elements 138. In some embodiments, the two outermost abrasive elements are about 1.5 mm in diameter and the inner abrasive elements are about 2.0 mm in diameter.

In the depicted embodiment, the one or more abrasive elements 138, individually, are oblong in shape. A variety of different shapes can be used for the one or more abrasive elements 138. For example, in some embodiments the one or more abrasive elements 138 are individually shaped as spheres, discs, rods, cylinders, polyhedrons, cubes, prisms, and the like. In some embodiments, such as the depicted embodiment, all of the one or more abrasive elements 138 are the same shape. In particular embodiments, one or more of the abrasive elements 138 has a different shape than one or more of the other abrasive elements 138. That is, two, three, or more differing shapes of individual abrasive elements 138 can be combined on the same drive shaft 136.

In the depicted embodiment, adjacent abrasive elements of the one or more abrasive elements 138 are spaced apart from each other. For example, in the depicted embodiment the two distal-most individual abrasive elements are spaced apart from each other by a distance 'X'. In some embodiments, the spacing between adjacent abrasive elements is consistent between all of the one or more abrasive elements 138. Alternatively, in some embodiments the spacing between some adjacent pairs of abrasive elements differs from the spacing between other adjacent pairs of abrasive elements.

In some embodiments, the spacing distance X in ratio to the maximum diameter of the abrasive elements 138 is about 1:1. That is, the spacing distance X is about equal to the maximum diameter. The spacing distance X can be selected to provide a desired degree of flexibility of the portion of the drive shaft 136 to which the one or more abrasive elements 138 are attached. In some embodiments, the ratio is about 1.5:1 (i.e., X is about 1.5 times longer than the maximum diameter). In some embodiments, the ratio is in a range of about 0.2:1 to about 0.4:1, or about 0.4:1 to about 0.6:1, or about 0.6:1 to about 0.8:1, or about 0.8:1 to about 1:1, or about 1:1 to about 1.2:1, or about 1.2:1 to about 1.4:1, or about 1.4:1 to about 1.6:1, or about 1.6:1 to about 1.8:1, or about 1.8:1 to about 2.0:1, or about 2.0:1 to about 2.2:1, or about 2.2:1 to about 2.4:1, or about 2.4:1 to about 3.0:1, or about 3.0:1 to about 4.0:1, and anywhere between or beyond those ranges.

In the depicted embodiment, the center of mass of each one of the one or more abrasive elements 138 is offset from the longitudinal axis of the drive shaft 136 along a same radial angle. Said another way, the centers of mass of all of the one or more abrasive elements 138 are coplanar with the longitudinal axis of the drive shaft 136. If the size of each of the one or more abrasive elements 138 is equal, the centers of mass of the one or more abrasive elements 138 would be collinear on a line that is parallel to the longitudinal axis of the drive shaft 136.

Referring to FIG. 15, according to some embodiments of the rotational atherectomy devices provided herein, one or more abrasive elements 144 are arranged at differing radial angles in relation to the drive shaft 136. In such a case, a path defined by the centers of mass of the one or more abrasive elements 144 spirals along the drive shaft 136. In some cases (e.g., when the diameters of the one or more abrasive elements 144 are equal and the adjacent abrasive elements are all equally spaced), the centers of mass of the one or more abrasive elements 144 define a helical path along/around the drive shaft 136. It has been found that such arrangements can provide a desirably-shaped orbital rotation of the one or more abrasive elements 144.

It should be understood that any of the structural features described in the context of one embodiment of the rotational atherectomy devices provided herein can be combined with any of the structural features described in the context of one or more other embodiments of the rotational atherectomy devices provided herein. For example, the size and/or shape features of the one or more abrasive elements 138 can be incorporated in any desired combination with the spiral arrangement of the one or more abrasive elements 144.

Figure 16:
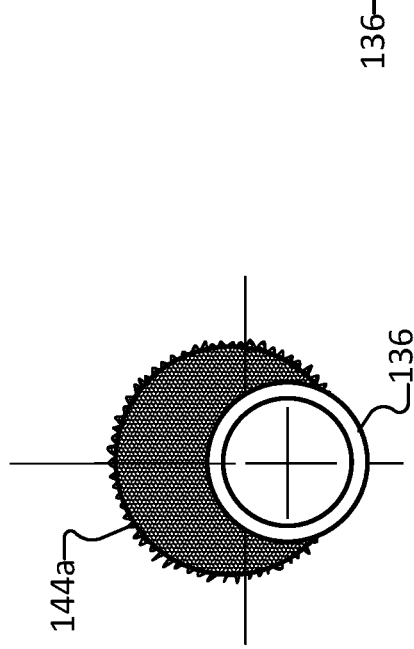
FIG. 16 is a transverse cross-sectional view of the rotational atherectomy device of FIG. 15 taken along the cutting-plane line 16-16.
Figure 20:
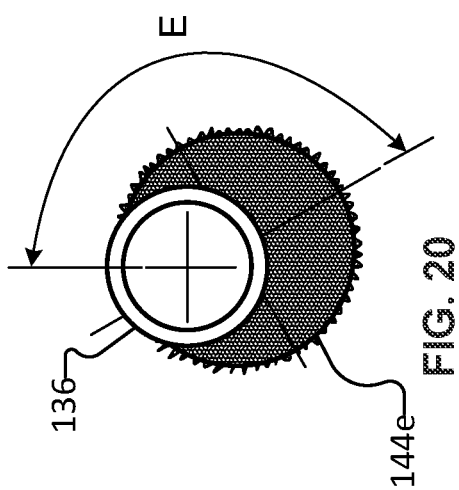
FIG. 20 is a transverse cross-sectional view of the rotational atherectomy device of FIG. 15 taken along the cutting-plane line 20-20.
Figure 19:
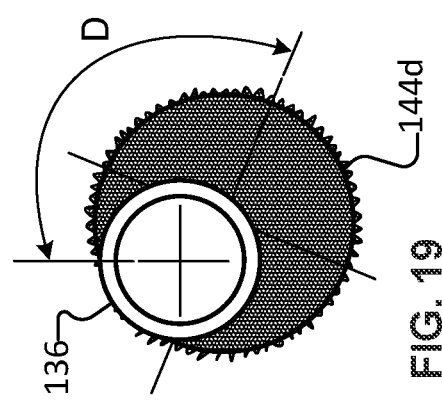
FIG. 19 is a transverse cross-sectional view of the rotational atherectomy device of FIG. 15 taken along the cutting-plane line 19-19.

Referring also to FIGS. 16-20, the differing radial angles of the individual abrasive elements 144a, 144b, 144c, 144d, and 144e can be further visualized. To avoid confusion, each figure of FIGS. 17-21 illustrates only the closest one of the individual abrasive elements 144a, 144b, 144c, 144d, and 144e (i.e., closest in terms of the corresponding cutting-plane as shown in FIG. 16). For example, in FIG. 17, abrasive element 144b is shown, but abrasive element 144a is not shown (so that the radial orientation of the abrasive element 144b is clearly depicted).

It can be seen in FIGS. 16-20 that the centers of mass of abrasive elements 144a, 144b, 144c, 144d, and 144e are at differing radial angles in relation to the drive shaft 136. Hence, it can be said that the abrasive elements 144a, 144b, 144c, 144d, and 144e are disposed at differing radial angles in relation to the drive shaft 136.

In the depicted embodiment, the radial angles of the abrasive elements 144a, 144b, 144c, 144d, and 144e differ from each other by a consistent 37.5 degrees (approximately) in comparison to the adjacent abrasive element(s). For example, the center of mass of abrasive element 144b is disposed at a radial angle B that is about 37.5 degrees different than the angle at which the center of mass of abrasive element 144a is disposed, and about 37.5 degrees different than the angle C at which the center of mass of abrasive element 144c is disposed. Similarly, the center of mass of abrasive element 144c is disposed at a radial angle C that is about 37.5 degrees different than the angle B at which the center of mass of abrasive element 144b is disposed, and about 37.5 degrees different than the angle D at which the center of mass of abrasive element 144d is disposed. The same type of relative relationships can be said about abrasive element 144d.

While the depicted embodiment has a relative radial offset of 37.5 degrees (approximately) in comparison to the adjacent abrasive element(s), a variety of other relative radial offsets are envisioned. For example, in some embodiments the relative radial offsets of the adjacent abrasive elements is in a range of about 0 degrees to about 5 degrees, or about 5 degrees to about 10 degrees, or about 10 degrees to about 15 degrees, or about 15 degrees to about 20 degrees, or about 20 degrees to about 25 degrees, or about 25 degrees to about 30 degrees, or about 30 degrees to about 35 degrees, or about degrees to about 30 degrees, or about 20 degrees to about 40 degrees, or about 20 degrees to about 50 degrees.

While in the depicted embodiment, the relative radial offsets of the abrasive elements 144a, 144b, 144c, 144d, and 144e in comparison to the adjacent abrasive element(s) are consistent, in some embodiments some abrasive elements are radially offset to a greater or lesser extent than others. For example, while angles B, C, D, and E are all multiples of 37.5 degrees, in some embodiments one or more of the angles B, C, D, and/or E is not a multiple of the same angle as the others.

The direction of the spiral defined by the centers of mass of the abrasive elements 144a, 144b, 144c, 144d, and 144e can be in either direction around the drive shaft 136, and in either the same direction as the wind of the filars or in the opposing direction as the wind of the filars.

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:

1. A method of rotationally abrading a material along an interior of an arteriovenous graft, the method comprising:

activating an electric motor housed within an actuator handle assembly positioned at a proximal end portion of a torque-transmitting coil to drive simultaneously rotation of an array of eccentric abrasive burrs within an interior of a synthetic arteriovenous graft at a rotational speed of 20,000 to 160,000 rpms so that at least one eccentric abrasive burr in the array travels in an orbital path having an orbit diameter multiple times greater than an outer maximum diameter of said at least one eccentric abrasive burr, the array of eccentric abrasive burrs being fixedly mounted to the torque-transmitting coil that defines a longitudinal axis extending in a longitudinal direction; and during said simultaneously rotating the array of eccentric abrasive burrs within the interior of the synthetic arteriovenous graft, slidably moving a carriage within a housing of the actuator handle assembly to reciprocate the array of eccentric abrasive burrs back and forth in the longitudinal direction within the interior of the synthetic arteriovenous graft, wherein the carriage is slidably movable in the longitudinal direction at the proximal end of the torque-transmitting coil;

wherein said slidably moving a carriage within a housing of the actuator handle assembly comprises moving the electric motor together with the carriage within the housing of the actuator handle assembly.

2. The method of claim 1, wherein during said simultaneously rotation of the array of eccentric abrasive burrs within the interior of the synthetic arteriovenous graft, simultaneously rotating a distal concentric metallic element along with the array of eccentric abrasive burrs within the interior of the synthetic arteriovenous graft, the distal concentric metallic element having an abrasive outer coating and being fixedly mounted to the torque-transmitting coil at a position distally of the array of eccentric abrasive burrs so that the distal concentric metallic element has a center of mass aligned with the longitudinal axis.

3. The method of claim 1, wherein the array of eccentric abrasive burrs are fixedly mounted to a distal end portion of the torque-transmitting coil such that a center of mass of each eccentric abrasive burr in the array is offset from the longitudinal axis.

4. The method of claim 3, wherein the array of eccentric abrasive burrs comprises a helical array such that a center of mass of each eccentric abrasive burr in the helical array is offset from the longitudinal axis and the centers of mass of the eccentric abrasive burrs in the helical array are arranged along a path that spirals around the longitudinal axis.

5. The method of claim 1, wherein the actuator handle assembly comprises an electrical switch to activate the electric motor to drive said rotation of the array of eccentric abrasive burrs within the interior of the synthetic arteriovenous graft at the rotational speed of 20,000 to 160,000 rpm.

6. The method of claim 5, wherein the electric motor of the actuator handle assembly is configured to modify the rotational speed of a drive shaft so as to modify the orbit diameter of the orbital path of the at least one eccentric abrasive burr in the array.

7. The method of claim 1, wherein each of eccentric abrasive burrs in the array has an outer diameter of 1.5 mm to 2.5 mm, and the synthetic arteriovenous graft has an outer diameter multiple times greater than a largest diameter of all of the eccentric abrasive burrs in the array.

8. The method of claim 1, wherein the array of eccentric abrasive burrs comprises five spherical abrasive burrs spaced apart from one another along the torque-transmitting coil.

9. A method of rotationally abrading a material along an interior of an arteriovenous graft, the method comprising:

activating an electric motor housed within an actuator handle assembly positioned at a proximal end portion of a torque-transmitting coil to drive simultaneously rotation of one or more eccentric abrasive burrs within an interior of a synthetic arteriovenous graft at a rotational speed of 20,000 to 160,000 rpms so that the one or more eccentric abrasive burrs travel in an orbital path having an orbit diameter multiple times greater than an outer maximum burr diameter of the one or more eccentric abrasive burrs, the one or more eccentric abrasive burrs being fixedly mounted to the torque-transmitting coil that defines a longitudinal axis extending in a longitudinal direction; and during said simultaneously rotating the one or more eccentric abrasive burrs within the interior of the synthetic arteriovenous graft, slidably moving a carriage within a housing of the actuator handle assembly to reciprocate the one or more eccentric abrasive burrs back and forth in the longitudinal direction within the interior of the synthetic arteriovenous graft, wherein the carriage is slidably movable in the longitudinal direction at the proximal end of the torque-transmitting coil;

wherein said slidably moving a carriage within a housing of the actuator handle assembly comprises moving the electric motor together with the carriage within the housing of the actuator handle assembly.

10. The method of claim 9, wherein during said simultaneously rotation of the one or more eccentric abrasive burrs within the interior of the synthetic arteriovenous graft, simultaneously rotating a distal concentric metallic element along with the one or more eccentric abrasive burrs within the interior of the synthetic arteriovenous graft, the distal concentric metallic element having an abrasive outer coating and being fixedly mounted to the torque-transmitting coil at a position distally of the one or more eccentric abrasive burrs so that the distal concentric metallic element has a center of mass aligned with the longitudinal axis.

11. The method of claim 9, wherein the one or more eccentric abrasive burrs comprises an array of eccentric abrasive burrs are fixedly mounted to a distal end portion of the torque-transmitting coil such that a center of mass of each eccentric abrasive burr in the array is offset from the longitudinal axis.

12. The method of claim 11, wherein the array of eccentric abrasive burrs comprises a helical array such that a center of mass of each eccentric abrasive burr in the helical array is offset from the longitudinal axis and the centers of mass of the eccentric abrasive burrs in the helical array are arranged along a path that spirals around the longitudinal axis.

13. The method of claim 9, wherein the actuator handle assembly comprises an electrical switch to activate the electric motor to drive said rotation of the one or more eccentric abrasive burrs within the interior of the synthetic arteriovenous graft at the rotational speed of 20,000 to 160,000 rpm.

14. The method of claim 9, wherein the electric motor of the actuator handle assembly is configured to modify the rotational speed of a drive shaft so as to modify the orbit diameter of the orbital path of the one or more eccentric abrasive burrs.

15. The method of claim 9, wherein each of the one or more eccentric abrasive burrs has an outer diameter of 1.5 mm to 2.5 mm, and the synthetic arteriovenous graft has an outer diameter multiple times greater than a largest diameter of all of the one or more eccentric abrasive burrs.

16. The method of claim 9, wherein the one or more eccentric abrasive burrs comprises five spherical abrasive burrs spaced apart from one another along the torque-transmitting coil.

* * * * *